US011701322B2

(12) United States Patent
Norman et al.

(10) Patent No.: US 11,701,322 B2
(45) Date of Patent: Jul. 18, 2023

(54) TOPICAL COMPOSITIONS AND METHODS

(71) Applicant: Mary Kay Inc., Addison, TX (US)

(72) Inventors: Greg Norman, Addison, TX (US);
David Gan, Southlake, TX (US);
Michelle Hines, Hickory Creek, TX (US); Lisha Vanpelt, Addison, TX (US); Wanli Zhao, Addison, TX (US); Barbara Durkee, Addison, TX (US); Lee Vickers, Addison, TX (US); Patricia Jacoby, Addison, TX (US)

(73) Assignee: MARY KAY INC., Addison, TX (US)

( * ) Notice: Subject to any disclaimer, the term of this patent is extended or adjusted under 35 U.S.C. 154(b) by 0 days.

(21) Appl. No.: 16/362,114

(22) Filed: Mar. 22, 2019

(65) Prior Publication Data
US 2019/0290575 A1 Sep. 26, 2019

Related U.S. Application Data

(60) Provisional application No. 62/799,528, filed on Jan. 31, 2019, provisional application No. 62/647,436, filed on Mar. 23, 2018.

(51) Int. Cl.
A61Q 19/00 (2006.01)
A61K 8/9789 (2017.01)
A61K 8/55 (2006.01)
A61K 8/34 (2006.01)
A61K 8/37 (2006.01)
A61K 8/44 (2006.01)
A61K 8/49 (2006.01)
A61Q 19/02 (2006.01)
A61K 8/60 (2006.01)
A61K 8/81 (2006.01)
A61K 8/891 (2006.01)
A61K 8/98 (2006.01)

(52) U.S. Cl.
CPC ............ A61K 8/9789 (2017.08); A61K 8/345 (2013.01); A61K 8/37 (2013.01); A61K 8/44 (2013.01); A61K 8/4926 (2013.01); A61K 8/55 (2013.01); A61K 8/602 (2013.01); A61K 8/8152 (2013.01); A61K 8/891 (2013.01); A61K 8/987 (2013.01); A61Q 19/007 (2013.01); A61Q 19/02 (2013.01)

(58) Field of Classification Search
CPC ..................................................... A61Q 19/02
See application file for complete search history.

(56) References Cited

U.S. PATENT DOCUMENTS

| | | |
|---|---|---|
| 2,798,053 A | 7/1957 | Brown |
| 4,509,949 A | 4/1985 | Huang et al. |
| 4,599,379 A | 7/1986 | Flesher et al. |
| 4,628,078 A | 12/1986 | Glover et al. |
| 4,835,206 A | 5/1989 | Farrar et al. |
| 4,849,484 A | 7/1989 | Heard |
| 5,087,445 A | 2/1992 | Haffey et al. |
| 5,100,660 A | 3/1992 | Hawe et al. |
| 5,254,331 A | 10/1993 | Mausner |
| 6,184,247 B1 | 2/2001 | Schneider |
| 6,503,490 B2 | 1/2003 | Johnson et al. |
| 6,936,280 B1 | 8/2005 | Lopez et al. |
| 7,105,184 B2 | 9/2006 | Pauly et al. |
| 7,803,354 B2 | 9/2010 | Biatry |
| 7,871,766 B2 | 1/2011 | Pauly et al. |
| 8,426,381 B2 | 4/2013 | Thibodeau et al. |
| 8,496,948 B2 | 7/2013 | Harripersad |
| 8,815,305 B2 | 8/2014 | Henry et al. |
| 9,233,061 B2 | 1/2016 | Jang et al. |
| 9,326,930 B2 | 5/2016 | Dreher |
| 9,327,007 B2 | 5/2016 | Park et al. |
| 9,364,413 B2 | 6/2016 | Lu et al. |
| 9,498,430 B1 | 11/2016 | Choi et al. |
| 9,511,144 B2 | 12/2016 | Jones et al. |
| 9,579,279 B2 | 2/2017 | Athwal |
| 9,827,178 B2 | 11/2017 | Desenne et al. |
| 9,925,137 B2 | 3/2018 | Stout et al. |
| 9,956,157 B2 | 5/2018 | Hwang et al. |
| 2004/0081672 A1 | 4/2004 | Gupta |
| 2004/0109905 A1 | 6/2004 | Bagchi |
| 2005/0163880 A1 | 7/2005 | Pusateri et al. |
| 2006/0216254 A1 | 9/2006 | Majmuda et al. |
| 2009/0148391 A1 | 6/2009 | Schmaus et al. |
| 2010/0303872 A1 | 12/2010 | Dumas et al. |
| 2013/0156873 A1* | 6/2013 | Florence ................ A61Q 19/02 424/757 |
| 2015/0064122 A1 | 3/2015 | Meyer et al. |

(Continued)

FOREIGN PATENT DOCUMENTS

| | | |
|---|---|---|
| CN | 1660081 | 8/2005 |
| CN | 101953764 | 1/2011 |

(Continued)

OTHER PUBLICATIONS

KR-100860605-B1 machine translation (Year: 2008).*
JP-S6322508-B2 machine translation (Year: 1988).*
KR-20100138307-A machine translation (Year: 2010).*
Prospector—George Deckner—Moisturizing Strategy: Tips and Recommendations for Formulation—Aug. 8, 2104, pp. 1-4 (Year: 2014).*
International Search Report and Written Opinion issued in Corresponding International Patent Application No. PCT/US2019/023619, dated Jul. 4, 2019.
Ma, Rui. "Making up following Rui MA" http://www.wenhuakxiyty. cn/dsrqw/book/base/14079269/568f6cd17074227e8d11bd65c2359841/ 5c3b58fdb028al01a75dc5a7979e829a.shtml?d. Jilin Science and Technology Press, Aug. 31, 2016, pp. 57, Accessed Sep. 2, 2022 (English Translation of relevant parts provided).

(Continued)

Primary Examiner — Lakshmi S Channavajjala
(74) Attorney, Agent, or Firm — Norton Rose Fulbright US LLP

(57) ABSTRACT

The present invention relates generally to methods of use and compositions useful for moisturizing skin and/or lightening or whitening skin. The composition includes a combination of *Angelica acutiloba* root extract and a *Salicornia herbacea* extract.

14 Claims, No Drawings

(56) References Cited

U.S. PATENT DOCUMENTS

| | | | |
|---|---|---|---|
| 2015/0250709 A1* | 9/2015 | Gan | A61K 8/31 424/62 |
| 2016/0220622 A1 | 8/2016 | Park et al. | |
| 2016/0303033 A1 | 10/2016 | Beyer et al. | |
| 2016/0354299 A1 | 12/2016 | Ershadi et al. | |
| 2017/0151172 A1 | 6/2017 | Shrivastava et al. | |
| 2017/0196780 A1 | 7/2017 | Mizuno et al. | |
| 2017/0281988 A1 | 10/2017 | Wu et al. | |

FOREIGN PATENT DOCUMENTS

| | | | |
|---|---|---|---|
| CN | 102018727 | | 4/2011 |
| CN | 102335216 | | 2/2012 |
| CN | 103998022 | | 8/2014 |
| CN | 104414869 | | 3/2015 |
| CN | 105343186 | | 2/2016 |
| CN | 105377300 | | 3/2016 |
| CN | 105708732 | | 6/2016 |
| CN | 106687102 | | 5/2017 |
| CN | 106880537 | | 6/2017 |
| CN | 107349167 | | 11/2017 |
| EP | 1321136 | | 6/2003 |
| EP | 3269356 A1 * | | 1/2018 ... A61K 8/98 |
| JP | S63-022508 | | 1/1988 |
| JP | 2001-106618 | | 4/2001 |
| JP | 2005330281 A * | | 12/2005 ... A61K 8/9728 |
| KR | 19990076491 | | 10/1999 |
| KR | 20010012902 | | 2/2001 |
| KR | 20020027834 | | 4/2002 |
| KR | 20030061835 | | 7/2003 |
| KR | 10-0447533 | | 8/2004 |
| KR | 20050040491 | | 5/2005 |
| KR | 20050077092 | | 8/2005 |
| KR | 1020050077092 A * | | 8/2005 |
| KR | 10-0561036 | | 3/2006 |
| KR | 20060023173 | | 3/2006 |
| KR | 10-0581747 | | 5/2006 |
| KR | 20060092258 | | 8/2006 |
| KR | 20080012958 | | 2/2008 |
| KR | 100860605 B1 * | | 9/2008 |
| KR | 10-0899502 | | 5/2009 |
| KR | 20100014948 | | 2/2010 |
| KR | 20100080440 | | 7/2010 |
| KR | 20100095973 | | 9/2010 |
| KR | 20100103708 | | 9/2010 |
| KR | 20100121709 | | 11/2010 |
| KR | 20100138307 | | 12/2010 |
| KR | 20110005746 | | 1/2011 |
| KR | 20110013812 | | 2/2011 |
| KR | 20110028286 | | 3/2011 |
| KR | 20110028309 | | 3/2011 |
| KR | 20110028599 | | 3/2011 |
| KR | 20110048378 | | 5/2011 |
| KR | 20110118497 | | 10/2011 |
| KR | 20060069472 | | 11/2011 |
| KR | 20120001597 | | 1/2012 |
| KR | 20120006722 | | 1/2012 |
| KR | 20120058724 | | 6/2012 |
| KR | 20120129601 | | 11/2012 |
| KR | 20130015565 | | 2/2013 |
| KR | 20130020964 | | 3/2013 |
| KR | 20130054210 | | 5/2013 |
| KR | 20130132548 | | 12/2013 |
| KR | 20140005204 | | 1/2014 |
| KR | 10-1363413 | | 2/2014 |
| KR | 20140040338 | | 4/2014 |
| KR | 20140071273 | | 6/2014 |
| KR | 20140073835 | | 6/2014 |
| KR | 20140102970 | | 8/2014 |
| KR | 20140103241 | | 8/2014 |
| KR | 20150064751 | | 6/2015 |
| KR | 20150065875 | | 6/2015 |
| KR | 20150132754 A * | | 11/2015 |
| KR | 20160003915 | | 1/2016 |
| KR | 20160003916 | | 1/2016 |
| KR | 20160017663 | | 2/2016 |
| KR | 20160021676 | | 2/2016 |
| KR | 20160049058 | | 5/2016 |
| KR | 20160052731 | | 5/2016 |
| KR | 20160068310 | | 6/2016 |
| KR | 20160068317 | | 6/2016 |
| KR | 20160078513 | | 7/2016 |
| KR | 10-1655407 | | 9/2016 |
| KR | 20160146779 | | 12/2016 |
| KR | 10-1719124 | | 3/2017 |
| KR | 20170033199 | | 3/2017 |
| KR | 20170038581 | | 4/2017 |
| KR | 20170076966 | | 7/2017 |
| KR | 20170086720 | | 7/2017 |
| KR | 10-1769416 | | 8/2017 |
| KR | 10-1769419 | | 8/2017 |
| KR | 10-1769422 | | 8/2017 |
| KR | 20170090830 | | 8/2017 |
| KR | 20170094478 | | 8/2017 |
| KR | 20170103086 | | 9/2017 |
| KR | 20170107828 | | 9/2017 |
| KR | 20170117234 | | 10/2017 |
| KR | 10-1796462 | | 11/2017 |
| KR | 20170135290 | | 12/2017 |
| KR | 10-1835486 | | 3/2018 |
| WO | WO 97/16155 | | 5/1997 |

OTHER PUBLICATIONS

Office Action and Search Report issued in Corresponding Chinese Application No. 201980034544.0, dated Sep. 19, 2022 (English Translation provided).

Pan, Xianglong. "1000 Questions of Traditional Chinese Medicine: Beauty" http://www.zhengzhifl.cn/n/dsrqw/book/base/10387696/abbd3a27b5174d8abb5f49e587b90138/4f910703d580d2b15a2de4c139ecf7ed.shtml?dm. Shanghai Science and Technology Press, Dec. 31, 2000, pp. 125, Accessed Sep. 2, 2022 (English Translation of relevant parts provided).

Uto, Takuhiro. "Anti-inflammatory Activity of Constituents Isolated from Aerial Part of Angelica acutiloba Kitagawa" *Phytotherapy Research 2015*, 29, 1956-1963.

Huang et al., "Characteristic Treatment Techniques in Cardiovascular Medicine" Scientific and Technical Documentation Press 2005, p. 885 (English Translation of relevant parts provided).

Li et al., "Effect of Taurine on the Expression of Matrix Metalloproteinases-3 in Brain Mantle of Rats with Diffuse Brain Injuries" Journal of Xinxiang Medical College 2010, 2, 123-126 (English Translation fo relevant parts provided).

Li et al., "New Techniques for Efficient Ecological Breeding of Freshwater Pearls" China Ocean Press 2014, 278-279 (English Translation of relevant parts proviced).

Mao, Qiuhua. Preliminary Study on Preparation and Biocompatibility of Nano scale Freshwater Pearl Powder. 2015. Master s Thesis of Central South University, p. 24, Chinese Doctoral Dissertations (English Translation of relevant parts proviced).

Huang et al., "Characteristic Treatment Techniques in Cardiovascular Medicine" Scientific and Technical Documentation Press 2005, p. 885.

Li et al., "Effect of Taurine on the Expression of Matrix Metalloproteinases-3 in Brain Mantle of Rats with Diffuse Brain Injuries" Journal of Xinxiang Medical College 2010, 2, 123-126.

Li et al., "New Techniques for Efficient Ecological Breeding of Freshwater Pearls" China Ocean Press 2014, 278-279.

Mao, Qiuhua. Preliminary Study on Preparation and Biocompatibility of Nano scale Freshwater Pearl Powder. 2015. Master s Thesis of Central South University, p. 24, Chinese Doctoral Dissertations.

Office Action and Search Report issued in Corresponding Chinese Application No. 201980034544.0, dated May 4, 2023 (English translations proviced).

* cited by examiner

TOPICAL COMPOSITIONS AND METHODS

CROSS-REFERENCE TO RELATED APPLICATIONS

The present application claims priority to U.S. provisional patent applications 62/647,436 filed Mar. 23, 2018, and 62/799,528 filed Jan. 31, 2019, the disclosures of which are hereby incorporated by reference in their entirety.

BACKGROUND OF THE INVENTION

A. Field of the Invention

The present invention relates generally to topical skin compositions that can be used to clean, moisturize, lighten, whiten, and/or used to improve the skin's condition and/or visual appearance. The compositions include a combination of skin active ingredients to achieve these effects. This combination includes *Angelica acutiloba* root extract and *Salicornia herbacea* extract to the skin, which has been found to work particularly well in whitening skin, reducing skin inflammation, and increasing skin moisture.

B. Description of Related Art

Ageing, chronic exposure to adverse environmental factors, malnutrition, fatigue, etc., can change the visual appearance, physical properties, or physiological functions of skin and tissue in ways that are considered visually undesirable. The most notable and obvious changes include the development of fine lines and wrinkles, loss of elasticity, increased sagging, loss of firmness, loss of color evenness or tone, coarse surface texture, and mottled pigmentation. Less obvious but measurable changes which occur as skin and tissue ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's and tissue's ability to remodel and repair itself. Many of the alterations in appearance and function of the skin are caused by changes in the outer epidermal layer of the skin, while others are caused by changes in the lower dermis.

The color in human skin is caused by the pigment melanin. Melanin is produced in special dendritic cells, melanocytes, which are found below or between the basal cells of the epidermis of the skin. When exposed to damaging environmental factors such the ultra violet (UV) radiation of the sun, irritants, and pollution, the keratinocyte (outermost cell of the skin) releases signaling molecules, such as $\alpha$-melanocyte-stimulating hormone ($\alpha$-MSH) and inflammatory cytokines, each of which can lead to unwanted skin pigmentation (e.g., hyperpigmented skin) and/or skin inflammation which is oftentimes characterized by reddened or erythemic skin, respectively. With respect to $\alpha$-MSH, this hormone can trigger melanocytes to produce excess melanin, thereby producing unwanted skin pigmentation. Many individuals have excess melanin pigmentation or a hyperpigmentation patch, which can cause pigmentary variation or abnormal pigmentation of the skin. This can lead to unwanted freckles or dark spots such as senile lentigo, liver spots, melasma, brown or age spots, vitiligo, sunburn pigmentation, post-inflammatory hyperpigmentation due to abrasion, burns, wounds or dermatitis, phototoxic reaction and other similar small, fixed pigmented lesions. It is often desirable to lighten these areas or even out the appearance of irregularly pigmented areas of skin to provide a more even looking skin tone/skin color. Individuals may also wish to increase fairness or reduce the overall level of pigmentation in the skin. In either case, the hyperpigmentation is usually viewed as cosmetically undesirable and individuals often wish to lighten the skin.

In some instances, the use of one skin lightening ingredient may not be effective for individuals with significant hyperpigmentation, freckles, or age spots, for example. Additionally, previous attempts to combine various skin lightening ingredients have been ineffective, and in some instance, have produced negative results such as exasperating the production of inflammatory cytokines.

Furthermore, previous attempts to improve the visual appearance of skin with known skin active-ingredients have been shown to have various drawbacks such as skin irritation and prolonged recovery periods. Maintaining moisture of the skin can help overcome some unwanted changes in skin. However, maintaining moisture of the skin can be difficult (e.g., is more dry than average). Exposure to chemicals, solvents, washing, cosmetics, fabrics, or dry environments are some of the many ways that skin can lose moisture.

Skin can lose moisture as a result of cleansing and/or freshening the skin. Skin cleansers and/or fresheners can be applied to skin and rinsed-off with water (e.g., rinse-off product), thereby, removing natural oils and lipids from the skin. Further, cleansers and/or fresheners oftentimes have ingredients that can be caustic to the skin. For instance, many types of cleansers and fresheners use certain surfactants that can cause skin irritation, which can lead to skin inflammation.

Skin can also lose moisture through the use of cosmetics. Cosmetics, including makeup foundations and masks, can cause drying of the skin. Foundations can be applied to skin and left on the skin so that additional makeup may be applied or to hide the appearance of unwanted blemishes or colors. Some problems associated with foundations include skin irritation, stability, lack of adequate effectiveness, difficulty in applying to skin, and drying of the skin. Masks are typically applied to skin and left on the skin for a period of time to allow the claimed benefits of the mask to occur. Problems associated with masks include skin irritation, stability, lack of adequate effectiveness, difficulty in applying to skin, and drying of the skin. Many masks also exfoliate the skin, which can cause or exasperate irritation, sensitivity, and dryness.

To address skin dryness, moisturizers have been developed. Moisturizers are complex mixtures of chemical agents specially designed to make the external layers of the skin (epidermis) softer and more pliable. They increase the skin's hydration (water content) by reducing evaporation. Naturally occurring skin lipids and sterols, as well as artificial or natural oils, humectants, emollients, lubricants, etc., can be part of the composition of commercial skin moisturizers. They usually are available as commercial products for cosmetic and therapeutic uses, but can also be made at home using common pharmacy ingredients. However, moisturizers are not perfect. Some problems associated with moisturizers include unpleasant tactile properties (e.g., heavy, greasy, or sticky feel), instability, skin-irritation, or insufficient moisturization capabilities.

SUMMARY OF THE INVENTION

The inventors have identified a solution to at least some of the problems associated with skin hyperpigmentation, skin inflammation, and/or skin in need of increased moisturization (e.g., dry skin). The solution is premised on a discovery of a combination of ingredients that can work together to modify certain biochemical pathways in the skin to reduce skin hyperpigmentation, reduce skin inflammation, and increase skin moisture levels. This combination can include an extract from *Angelica acutiloba* root, preferably an aqueous extract where water is used as the extracting solvent, and an extract from *Salicornia herbacea*, preferably a supercritical extract using carbon dioxide ($CO_2$) as the extracting medium. In particular, it was discovered that *Angelica acutiloba* root extract has a tertiary ability to (1) decrease tyrosinase activity in melanocytes, which can lead to reduction in melanin production in skin, thereby whitening or lightening skin, (2) decrease interleukin-6 (IL-6) production in skin (e.g., epidermal keratinocytes, fibroblasts, and/or dermal endothelial cells), which can reduce the inflammatory pathway and ultimately reduce skin inflammation, and (3) reduce oxidation in skin by acting as an anti-oxidant. Still further, it was also discovered that *Salicornia herbacea* extract can increase aquaporin 3 (AQP3) expression in skin (e.g., epidermal keratinocytes), which can be beneficial in treating dry skin or skin that is in need of increased moisturization, as AQP3 can act as a membrane transporter of water and glycerol expressed in plasma membranes in the basal layer of keratinocytes of the epidermis. In addition, it was discovered that niacinamide can be combined safely with *Angelica acutiloba* root *Salicornia herbacea* extracts without negatively affecting the aforementioned skin efficacy abilities of either of the extracts. Further, niacinamide can remain structural stable in the presence of these extracts and can reduce melanin production in melanocytes, thereby providing an additional skin whitening or lightening effect. Still further, additional combinations of ingredients, which are discussed below, are also contemplated in the context of the present invention to be beneficial for skin (e.g., fine lines or wrinkles, sagging skin, skin having reduced elasticity, etc.).

In one aspect of the present invention there is disclosed a topical skin composition that includes any one of, any combination of, or all of an effective amount of an *Angelica acutiloba* root extract, a *Salicornia herbacea* extract, or niacinamide, and a cosmetic vehicle. The amounts of the ingredients within the composition can vary (e.g., amounts can be as low as 0.000001% to as high as 98% w/w or any range therein). In some aspects, the topical composition includes the composition can include 0.001 to 5%, preferably 0.001 to 2%, or more preferably 0.001 to 1%, or even more preferably 0.001 to 0.1% by weight of *Angelica acutiloba* root extract, 0.001 to 5%, preferably 0.001 to 2%, or more preferably 0.001 to 1%, or even more preferably 0.001 to 0.1% by weight *Salicornia herbacea* extract, and optionally 0.001 to 5%, preferably 0.001 to 2%, or more preferably 0.001 to 1%, or even more preferably 0.001 to 0.5% by weight niacinamide, and optionally 99.3 to 99.997% by weight cosmetic vehicle. In some instances, the *Angelica acutiloba* root extract is an aqueous extract and the *Salicornia herbacea* extract is a supercritical carbon dioxide ($CO_2$) extract.

In some instances, the topical composition includes water. In some instances, the composition includes 25 to 90% by weight of water. In some instances, the topical composition is a solution, an emulsion, a serum, a gel, a gel emulsion, or a gel serum. In some instances, the topical composition is a lotion, cream, butter, wash, or scrub. In some instances, the topical composition is a cream-gel suitable for application to the under eye area. Other topical compositions of the present invention can be used to cleanse and/or freshen the skin without drying the skin. In some instances, the composition is applied to dry or erythemic skin. In some instances, the composition is applied to hyperpigmented skin or melisma. In some instances, the hyperpigmented skin or melisma is a freckle or a dark spot. In some instances, the composition is applied to skin in need of moisturization and in need of whitening.

In some instances, the topical composition is capable of moisturize and/or lightening or whitening of skin. In some instances, the topical composition includes an effective amount of: (1) *Angelica acutiloba* root extract to decrease tyrosinase expression, reduce oxidative damage in skin caused by free-radicals, and/or reduce IL-6 expression in skin and thus reduce skin inflammation; (2) *Salicornia herbacea* extract to increase aquaporin 3 (AQP3) expression in skin to increase skin moisture in skin in need of moisturization; and optionally (3) niacinamide to reduce melanin production in melanocytes. In some instances, the topical composition includes an effective amount of *Angelica acutiloba* root extract, *Salicornia herbacea* extract, and niacinamide capable of increasing skin moisture, increasing production of occluding, inhibiting TNF-α production, increase production of filaggrin/urea, and/or preventing oxidative damage. In some instances, the topical composition includes an effective amount of *Salicornia herbacea* extract to inhibit tryosinase activity and decrease the production of melanin. In some instances, the topical composition includes an effective amount of *Angelica acutiloba* root extract to promote collagen synthesis and inhibit collagen degradation. In some instances, the topical composition includes an effective amount of niacinamide to decrease the production of melanin. In some instances, the topical composition includes an effective amount of an ascorbyl compound (e.g., sodium ascorbyl phosphate or ascorbyl glucoside) to inhibit melanin production in melanocytes, to reduce tyrosinase activity in skin, to reduce oxidative damage in skin caused by free radicals, to increase collagen-1 expression in skin which can help with reducing the appearance of wrinkles and fine lines and reduce the appearance of sagging or non-elastic skin, to increase lysyl oxidase expression in skin, which can help with reducing the appearance of wrinkles and fine lines and reduce the appearance of sagging or non-elastic skin by increasing cross-linking of collagens and elastin, and/or reduce expression of TNF-α and lipoxygenase in skin, which can help reduce skin inflammation (e.g., reddened or erythemic skin, sensitive skin, etc.). In some instances, the composition includes an effective amount of sodium ascorbyl phosphate and/or ascorbyl glucoside to decrease tyrosinase activity in the skin, decrease melanin production in the skin, reduce oxidation of the skin, increase collagen-1 expression in the skin, increase lysyl oxidase in the skin, and/or reduce TNF-α and lipoxygenase activity in the skin. In some instances, the composition includes 0.0001 to 5%, preferably 0.0001 to 3%, or more preferably 0.001 to 2% by weight of sodium ascorbyl phosphate and/or ascrobyl glucoside. In some instances, the composition includes an additional skin whitening or lightening agent (e.g., phenylethyl resorcinol and/or vegetable amino acids such as navy bean extract) to reduce tyrosinase activity and to reduce melanin production in melanocytes. In some instances, the composition can include 0.0001 to 5%, preferably 00001 to 2%, or more preferably 0001 to 1% by weight of vegetable amino acids from navy bean. In some instances, the topical composition can include an effective amount of hydrolyzed pearl extract to promote the healing of blemishes and other skin problems and/or help even skin tone by decreasing age spots, freckles, discoloration and acne through reduction of tyrosinase activity and reduction in melanin production in melanocytes. Hydrolyzed pearl extract can also be used to inhibit matrix metalloprotease-9 (MMP-9) production in skin, which can help reduce the appearance of fine lines or wrinkles. MMP-9 enzymes are extracellular proteases that can degrade important skin structural proteins such as collagen VII, fibronectins, and laminin. In some instances, the composition includes 0.0001 to 5%, preferably 0.0001 to 2%, more preferably 0.001 to 1% by weight of hydrolyzed pearl extract. In some instances, the composition includes 10 to 99%, preferably 20 to 95%, more preferably 25 to 90% by weight of water.

The topical compositions disclosed herein may further contain one or more ingredients described herein. For example, the composition may contain one or more additional ingredients selected from one or more conditioning agents, moisturizing agents, pH adjusters, structuring agents, inorganic salts, and preservatives. In some instances, the composition further contains glycerin, butylene glycol, caprylic/capric triglycerides, acrylates/C10-30 alkyl acrylate crosspolymer, dimethicone and 1,2-hexanediol. In some instances, the composition 1 to 15% by weight glycerin, 0.1 to 5% by weight butylene glycol, 0.1 to 1.5% by weight caprylic/capric triglyceride, 0.1 to 1% by weight acrylates/C10-30 alkyl acrylate crosspolymer, 0.1 to 10% by weight dimethicone, and 0.1 to 1.5% by weight 1, 2-hexanediol. In some instances, the composition includes ammonium acryloyldimethyltaurate/VP copolymer (e.g., 0.1 to 1% by weight of ammonium acryloyldimethyltaurate/VP copolymer). In some instances, the composition further contains silica, polyacrylamide, C13-14 isoparaffins and Laureth-7. In some instances, the composition contains 0.1 to 5% by weight silica, 0.1 to 1% by weight polyacrylamide, 0.1 to 1% by weight C13-14 isoparaffins and 0.001 to 0.15% by weight Laureth-7. In some instances, the composition contains glycerin, potassium stearate, dipropylene glycol, sorbitol, potassium myristate, myristic acid, glyceryl stearate SE, PEG-60 glyceryl isosterate, steric acid, sodium methyl cocyl taurate, PEG-32, potassium laurate, glycol stearate, butylene glycol, and poly(acrylamide-co-diallyldimethylammonium chloride). In some instances, the composition can include 1 to 25% by weight glycerin, 5 to 20% by weight potassium stearate, 1 to 10% by weight dipropylene glycol, 1 to 10% by weight sorbitol, 1 to 5% by weight potassium myristate, 1 to 5% by weight myristic acid, 1 to 5% by weight glyceryl stearate SE, 1 to 5% by weight PEG-60 glyceryl isosterate, 1 to 5% by weight steric acid, 1 to 3% by weight sodium methyl cocyl taurate, 1 to 3% by weight PEG-32, 1 to 5% by weight potassium laurate, 0.1 to 3% by weight glycol stearate, 0.1 to 2% by weight butylene glycol, 0.1 to 1% by weight poly(acrylamide-co-diallyldimethylammonium chloride), and 0.1 to 1% by weight lauric acid. In some instances, the topical composition can include *Opuntia tuna* fruit extract. By way of example, the topical composition can include 0.0001 to 0.15% *Opuntia tuna* fruit extract. In some instances, the composition can include 1 to 15% by weight glycerin, 0.1 to 5% by weight butylene glycol, 0.1 to 5% by weight polyethylene glycol (PEG)-75, 0.1 to 5% by weight propanediol, and 0.1 to 1% by weight pentylene glycol. In some instances, the composition is an emulsion, serum, gel, gel emulsion, gel serum, a cream, a cream-gel, a lotion, or a solution.

In some embodiments, a topical skin composition can include water, an aqueous extract of *Angelica acutiloba* root, a *Salicornia herbacea* extract, niacinamide, sodium ascorbyl phosphate, phenylethyl resorcinol, hydrolyzed pearl extract, glycerin, propandiol, butylene glycol, caprylic/capric triglyceride, acrylates/C10-30 alkyl acrylate crosspolymer, dimethicone, 1,2-hexanediol, isodecyl neopentanoate, petrolatum, PEG-60 glyceryl isosterate, cetyl ethylhexanoate, sorbitol, and ammonium acryloyldimethyltaurate/VP copolymer. This topical skin composition can be a lotion.

In some embodiments, a topical skin composition can include water, an aqueous extract of *Angelica acutiloba* root, a *Salicornia herbacea* extract, niacinamide, sodium ascorbyl phosphate, vegetable amino acids (e.g., navy bean extract), glycerin, propandiol, butylene glycol, caprylic/capric triglyceride, acrylates/C10-30 alkyl acrylate crosspolymer, dimethicone, 1, 2-hexanediol, triethanolamine, disodium ethylenediaminetetraacetic acid, silica, and ammonium acryloyldimethyltaurate/VP copolymer. This topical skin composition can be formulated as a serum. In some instances, the composition includes *Angelica acutiloba* root extract, *Salicornia herbacea* extract, niacinamide, and a cosmetic vehicle, and is capable of conditioning skin, whitening skin or lightening skin, or any combination thereof. In some instances, the composition moisturizes skin. In some instances, the composition includes *Angelica acutiloba* root extract, *Salicornia herbacea* extract, niacinamide, and a cosmetic vehicle, and is capable of cleaning skin, conditioning skin, or whitening skin, or any combination thereof. In some instances, the composition includes 0.001 to 0.1% by weight of *Angelica acutiloba* root extract, 0.001 to 0.1% by weight *Salicornia herbacea* extract, 0.001 to 0.5% by weight niacinamide, and 99.3 to 99.997% by weight cosmetic vehicle.

In another aspect, a topical skin composition can include water, an aqueous extract of *Angelica acutiloba* root, a *Salicornia herbacea* extract, niacinamide, sodium ascorbyl phosphate and/or ascorbyl glucoside, vegetable amino acids (e.g., navy bean extract), hydrolyzed pearl extract, glycerin, butylene glycol, caprylic/capric triglyceride, acrylates/C10-30 alkyl acrylate crosspolymer, dimethicone, butylene glycol, 1, 2-hexanediol, polyacrylamide, C13-14 isoparaffins, caprylyl glycol, Laureth-7, triethanolamine, octyldodecanol, dimethicone; and dipotassium glycyrrhizate. This formulation can be a cream-gel emulsion and, in some instances, be used under the eye to moisturize the skin beneath the eye. In some embodiments, the topical skin composition can include water, an aqueous extract of *Angelica acutiloba* root, a *Salicornia herbacea* extract, niacinamide, sodium ascorbyl phosphate and/or ascorbyl glucoside, phenylethyl resorcinol, hydrolyzed pearl extract, glycerin, butylene glycol, caprylic/capric triglyceride, acrylates/C10-30 alkyl acrylate crosspolymer, dimethicone, propandiol, 1,2-hexanediol, isodecyl neopentanoate, petrolatum, PEG-60 glyceryl isosterate, cetyl ethylhexanoate, sorbitol, and ammonium acryloyldimethyltaurate/VP copolymer. In some instances, the composition can include water, an aqueous extract of *Angelica acutiloba* root, a *Salicornia herbacea* extract, niacinamide, sodium ascorbyl phosphate and/or ascorbyl glucoside, vegetable amino acids, glycerin, propandiol, butylene glycol, caprylic/capric triglyceride, acrylates/C10-30 alkyl acrylate crosspolymer, dimethicone, 1, 2-hexanediol, triethanolamine, disodium ethylenediaminetetraacetic acid, silica, and ammonium acryloyldimethyltaurate/VP copolymer. In some instances, the composition can include water, an aqueous extract of *Angelica acutiloba* root, *Salicornia herbacea* extract, niacinamide, sodium ascorbyl phosphate and/or ascorbyl glucoside, vegetable amino acids, hydrolyzed pearl extract, glycerin, butylene glycol, caprylic/capric triglyceride, acrylates/C10-30 alkyl acrylate crosspolymer, dimethicone, butylene glycol, 1, 2-hexanediol, polyacrylamide, C13-14 isoparaffins, caprylyl glycol, Laureth-7, triethanolamine, octyldodecanol, dimethicone, and dipotassium glycyrrhizate. In some instances, the composition includes water, an aqueous extract of *Angelica acutiloba* root, a *Salicornia herbacea* extract, niacinamide, potassium ascorbyl phosphate and/or ascorbyl glucoside, vegetable amino acids, hydrolyzed pearl extract, glycerin, butylene glycol, polyethylene glycol (PEG)-75, propanediol, pentylene glycol, caprylic/capric triglyceride, phenoxyethanol, disodium ethylenediaminetetraacetic acid, sodium hylauronate, and triethanolamine. In some instances, the composition includes water, an aqueous extract of *Angelica acutiloba* root, a *Salicornia herbacea* extract, niacinamide, sodium ascorbyl phosphate and/or ascorbyl glucoside, vegetable amino acids, hydrolyzed pearl extract, glycerin, potassium stearate, dipropylene glycol, sorbitol, potassium myristate, myristic acid, glyceryl stearate SE, PEG-60 glyceryl isosterate, steric acid, sodium methyl cocyl taurate, PEG-32, potassium laurate, glycol stearate, butylene glycol, poly(acrylamide-co-diallyldimethylammonium chloride), and lauric acid.

In still another aspect of the invention, a topical skin composition can include water, an aqueous extract of *Angelica acutiloba* root, a *Salicornia herbacea* extract, niacinamide, potassium ascorbyl phosphate, vegetable amino acids (e.g., navy bean extract), hydrolyzed pearl extract, glycerin, butylene glycol, polyethylene glycol-75, propanediol, pentylene glycol, caprylic/capric triglyceride, acrylates/C10-30 alkyl acrylate crosspolymer, dimethicone, butylene glycol, phenoxyethanol, disodium ethylenediaminetetraacetic acid, sodium hylauronate, and triethanolamine. This topical skin composition can be formulated as a solution that can be applied to the skin to freshen, hydrate, and/or lighten or whitening the skin.

In yet another aspect, a topical skin composition can include water, an aqueous extract of *Angelica acutiloba* root, a *Salicornia herbacea* extract, niacinamide, potassium ascorbyl phosphate, amino acids (e.g., navy bean extract), hydrolyzed pearl extract, glycerin, potassium stearate, dipropylene glycol, sorbitol, potassium myristate, myristic acid, glyceryl stearate SE, PEG-60 glyceryl isosterate, steric acid, sodium methyl cocyl taurate, PEG-32, potassium laurate, glycol stearate, butylene glycol, poly(acrylamide-co-diallyldimethylammonium chloride), and lauric acid. This topical composition can be formulated a cleanser for the skin.

Methods of use of the compositions disclosed herein are also disclosed. In some aspects, a method is disclosed of improving a condition or appearance of skin comprising topically applying any one of the compositions of the present invention to skin and/or face in need thereof. In one aspect, any one of the compositions disclosed herein are topically applied and the composition is left on the application area, removed from the application area after a period of time (e.g., lotion, serum, toner, or cream), and/or removed directly after application (e.g., cleanser or toner).

In some aspects, the compositions of the present invention are used to promote hydration, cleansing, and/or whitening or lightening of skin. In some aspects, the compositions disclosed here are used to condition skin (e.g., hydrate skin). In some instances, the compositions disclosed herein are used to reduce melanin production in skin, reduce tyrosinase production in skin, increase aquaporin 3 production in skin, reduce oxidation of skin components from reactive oxygen species (ROS), increase collagen 1 production in skin, reduce MMP-9 production in skin, increase lysyl oxidase production in skin, reduce TNF-α production in skin, reduce lipoxygenase production in skin, and/or reduce IL-6 production in skin (e.g., epidermal keratinocytes, melanocytes, fibroblasts, and/or dermal endothelial cells).

In particular aspects, the compositions of the present invention are formulated as a topical composition. The composition can have a dermatologically acceptable vehicle or carrier for the compounds and extracts. The composition can further include a moisturizing agent or a humectant, a surfactant, a silicone containing compounds, a UV agent, an oil, and/or other ingredients identified in this specification or those known in the art. The composition can be a lotion, cream, body butter, mask, scrub, wash, gel, serum, emulsion (e.g., oil-in-water, water-in-oil, silicone-in-water, water-in-silicone, water-in-oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, gel serums, gel emulsions, etc. The composition can be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In some aspects, the triglyceride is a medium chain triglyceride (e.g., caprylic capric triglyceride). The compositions can also include preservatives. Non-limiting examples of preservatives include potassium benzoate, sorbic acid, potassium sorbate, phenoxyethanol, methylparaben, propylparaben, or any mixture thereof. In some embodiments, the composition is paraben-free.

Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, mist, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse off composition can be a skin cleanser, shampoo, conditioner, or soap. An example of a leave-on composition can be a skin moisturizer, sunscreen, mask, overnight cream, serum, or a day cream.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a gel, a wash, a body butter, a scrub, a foundation, a night cream, a lipstick, a cleanser, a toner, a sunscreen, a mask, an anti-aging product, a deodorant, an antiperspirant, a perfume, a cologne, etc.

Also disclosed are the following Embodiments 1 to 54 of the present invention. Embodiment 1 is a method of moisturizing skin or whitening skin, the method comprising topically applying to skin in need thereof a composition comprising an effective amount of an *Angelica acutiloba* root extract to reduce tyrosinase activity in the skin to whiten the skin and to optionally reduce interleukin-6 (IL-6) activity in skin to reduce skin inflammation, and an effective amount of a *Salicornia herbacea* extract to increase expression of aquaporin 3 (AQP3) in the skin to moisturize the skin. Embodiment 2 is the method of Embodiment 1, wherein the *Angelica acutiloba* root extract is an aqueous extract and the *Salicornia herbacea* extract is a supercritical carbon dioxide ($CO_2$) extract. Embodiment 3 is the method of any one of Embodiments 1 to 2, wherein the composition comprises 0.001 to 1% by weight of the *Angelica acutiloba* root extract and 0.001 to 1% by weight of the *Salicornia herbacea* extract. Embodiment 4 is the method of any one of Embodiments 1 to 3, wherein the composition is applied to dry or erythemic skin. Embodiment 5 is the method of any one of Embodiments 1 to 4, wherein the composition is applied to hyperpigmented skin or melasma. Embodiment 6 is the method of Embodiment 5, wherein the hyperpigmented skin or melasma is a freckle or a dark spot. Embodiment 7 is the method of any one of Embodiments 1 to 6, wherein the composition is applied to skin in need of moisturization and in need of whitening. Embodiment 8 is the method of any one of Embodiments 1 to 7, wherein the composition further comprises an effective amount of niacinamide, preferably 0.001 to 1% by weight of niacinamide, to decrease melanin production in the skin. Embodiment 9 is the method of any one of Embodiments 1 to 8, wherein the composition comprises an effective amount of sodium ascorbyl phosphate and/or ascorbyl glucoside to decrease tyrosinase activity in the skin, decrease melanin production in the skin, reduce oxidation of the skin, increase collagen-1 expression in the skin, increase lysyl oxidase in the skin, and/or reduce TNF-alpha and lipoxygenase activity in the skin. Embodiment 10 is the method of Embodiment 9, wherein the composition comprises 0.001 to 2% by weight of the sodium ascorbyl phosphate and/or ascorbyl glucoside. Embodiment 11 is the method of any one of Embodiments 1 to 10, wherein the composition further comprises vegetable amino acids from navy bean to reduce tyrosinase activity and/or reduce melanin production in the skin. Embodiment 12 is the method of Embodiment 11, wherein the composition comprises 0.001 to 1% by weight of the vegetable amino acids from navy bean. Embodiment 13 is the method of any one of Embodiments 1 to 12, wherein the composition further comprises hydrolyzed pearl extract to reduce tyrosinase activity, reduce melanin production, and/or reduce MMP-9 activity in the skin. Embodiment 14 is the method of Embodiment 13, wherein the composition comprises 0.001 to 1% by weight of the hydrolyzed pearl extract. Embodiment 15 is the method of any one of Embodiments 1 to 14, wherein the composition further comprises 25 to 90% by weight of water. Embodiment 16 is the method of any one of Embodiments 1 to 15, wherein the composition further comprises glycerin, butylene glycol, caprylic/capric triglyceride, acrylates/C10-30 alkyl acrylate crosspolymer, 1,2-hexanediol, and dimethicone. Embodiment 17 is the method of Embodiment 16, wherein the composition comprises 1 to 15% by weight glycerin, 0.1 to 5% by weight butylene glycol, 0.1 to 1.5% by weight caprylic/capric triglyceride, 0.1 to 1% by weight acrylates/C10-30 alkyl acrylate crosspolymer, 0.1 to 10% by weight dimethicone, and 0.1 to 1.5% by weight 1, 2-hexanediol. Embodiment 18 is the method of Embodiments 16 to 17, wherein the composition further comprises 0.1 to 1% by weight of ammonium acryloyldimethyltaurate/VP copolymer. Embodiment 19 is the method of any one of Embodiments 16 to 18, wherein the composition further comprises 0.1 to 5% by weight silica, 0.1 to 1% by weight polyacrylamide, 0.1 to 1% by weight C13-14 isoparaffin; and 0.001 to 0.15% by weight Laureth-7. Embodiment 20 is the method of any one of Embodiments 1 to 15, wherein the topical composition further comprises 1 to 15% by weight glycerin, 0.1 to 5% by weight butylene glycol, 0.1 to 5% by weight polyethylene glycol (PEG)-75, 0.1 to 5% by weight propanediol, and 0.1 to 1% by weight pentylene glycol. Embodiment 21 is the method of any one of Embodiments 1 to 15, wherein the topical composition further comprises 1 to 25% by weight glycerin, 5 to 20% by weight potassium stearate, 1 to 10% by weight dipropylene glycol, 1 to 10% by weight sorbitol, 1 to 5% by weight potassium myristate, 1 to 5% by weight myristic acid, 1 to 5% by weight glyceryl stearate SE, 1 to 5% by weight PEG-60 glyceryl isosterate, 1 to 5% by weight steric acid, 1 to 3% by weight sodium methyl cocyl taurate, 1 to 3% by weight PEG-32, 1 to 5% by weight potassium laurate, 0.1 to 3% by weight glycol stearate, 0.1 to 2% by weight butylene glycol, 0.1 to 1% by weight poly(acrylamide-co-diallyldimethylammonium chloride), and 0.1 to 1% by weight lauric acid. Embodiment 22 is the method of any one of Embodiments 1 to 21, wherein the topical composition is an emulsion, serum, gel, gel emulsion, gel serum, a cream, a cream-gel, a lotion, or a solution. Embodiment 23 is a topical skin composition capable of whitening skin or moisturizing skin, the composition comprising an effective amount of an *Angelica acutiloba* root extract to reduce tyrosinase activity in the skin to whiten the skin and to optionally reduce interleukin-6 (IL-6) activity in skin to reduce skin inflammation, and an effective amount of a *Salicornia herbacea* extract to increase expression of aquaporin 3 (AQP3) in the skin to moisturize the skin. Embodiment 24 is the topical skin composition of Embodiment 23, wherein the *Angelica acutiloba* root extract is an aqueous extract and the *Salicornia herbacea* extract is a supercritical carbon dioxide ($CO_2$) extract. Embodiment 25 is the topical skin composition of any one of Embodiments 23 to 24, wherein the wherein the composition comprises 0.001 to 1% by weight of the *Angelica acutiloba* root extract and 0.001 to 1% by weight of the *Salicornia herbacea* extract. Embodiment 26 is the topical skin composition of any one of Embodiments 23 to 25, further comprising 0.001 to 1% by weight of niacinamide to reduce tyrosinase activity or reduce melanin production in skin. Embodiment 27 is the topical skin composition of Embodiment 23, wherein the composition comprises 0.001 to 0.1% by weight of *Angelica acutiloba* root extract, 0.001 to 0.1% by weight *Salicornia herbacea* extract, 0.001 to 0.5% by weight niacinamide, and 99.3 to 99.997% by weight cosmetic vehicle. Embodiment 28 is the topical skin composition of any one of Embodiments 23 to 27, wherein the composition comprises an effective amount of sodium ascorbyl phosphate and/or ascorbyl glucoside to decrease tyrosinase activity in the skin, decrease melanin production in the skin, reduce oxidation of the skin, increase collagen-1 expression in the skin, increase lysyl oxidase in the skin, and/or reduce TNF-alpha and lipoxygenase activity in the skin. Embodiment 29 is the topical skin composition of Embodiment 28, wherein the composition comprises 0.001 to 2% by weight of the sodium ascorbyl phosphate and/or ascorbyl glucoside. Embodiment 30 is the topical skin composition of any one of Embodiments 23 to 29, further comprising vegetable amino acids from navy bean to reduce tyrosinase activity and/or reduce melanin production in the skin. Embodiment 31 is the topical skin composition of Embodiment 30, wherein the composition comprises 0.001 to 1% by weight of the vegetable amino acids from navy bean. Embodiment 32 is the topical skin composition of any one of Embodiments 23 to 31, further comprising hydrolyzed pearl extract to reduce tyrosinase activity, reduce melanin production, and/or reduce MMP-9 activity in the skin. Embodiment 33 is the topical skin composition of Embodiment 32, wherein the composition comprises 0.001 to 1% by weight of the hydrolyzed pearl extract. Embodiment 34 is the topical skin composition of any one of Embodiments 23 to 33, further comprising 25 to 90% by weight of water. Embodiment 35 is the topical skin composition of any one of Embodiments 23 to 34, wherein the composition further comprises glycerin, butylene glycol, caprylic/capric triglyceride, acrylates/ C10-30 alkyl acrylate crosspolymer, 1,2-hexanediol, and dimethicone. Embodiment 36 is the topical skin composition of Embodiment 35, wherein the composition comprises 1 to 15% by weight glycerin, 0.1 to 5% by weight butylene glycol, 0.1 to 1.5% by weight caprylic/capric triglyceride, 0.1 to 1% by weight acrylates/C10-30 alkyl acrylate crosspolymer, 0.1 to 10% by weight dimethicone, and 0.1 to 1.5% by weight 1, 2-hexanediol. Embodiment 37 is the topical skin composition of any one of Embodiments 35 to 36, wherein the composition further comprises 0.1 to 1% by weight of ammonium acryloyldimethyltaurate/VP copolymer. Embodiment 38 is the topical skin composition of any one of Embodiments 35 to 37, wherein the composition further comprises 0.1 to 5% by weight silica, 0.1 to 1% by weight polyacrylamide, 0.1 to 1% by weight C13-14 isoparaffin; and 0.001 to 0.15% by weight Laureth-7. Embodiment 39 is the topical skin composition of any one of Embodiments 23 to 38, wherein the topical composition further comprises 1 to 15% by weight glycerin, 0.1 to 5% by weight butylene glycol, 0.1 to 5% by weight polyethylene glycol (PEG)-75, 0.1 to 5% by weight propanediol, and 0.1 to 1% by weight pentylene glycol. Embodiment 40 is the topical skin composition of any one of Embodiments 23 to 39, wherein the topical composition further comprises 1 to 25% by weight glycerin, 5 to 20% by weight potassium stearate, 1 to 10% by weight dipropylene glycol, 1 to 10% by weight sorbitol, 1 to 5% by weight potassium myristate, 1 to 5% by weight myristic acid, 1 to 5% by weight glyceryl stearate SE, 1 to 5% by weight PEG-60 glyceryl isosterate, 1 to 5% by weight steric acid, 1 to 3% by weight sodium methyl cocyl taurate, 1 to 3% by weight PEG-32, 1 to 5% by weight potassium laurate, 0.1 to 3% by weight glycol stearate, 0.1 to 2% by weight butylene glycol, 0.1 to 1% by weight poly(acrylamide-co-diallyldimethylammonium chloride), and 0.1 to 1% by weight lauric acid. Embodiment 41 is the topical skin composition of any one of Embodiments 23 to 40, wherein the topical composition is an emulsion, serum, gel, gel emulsion, gel serum, a cream, a cream-gel, a lotion, or a solution. Embodiment 42 is the topical skin composition of any one of Embodiments 23 to 41, further comprising *Opuntia tuna* fruit extract. Embodiment 43 is the topical skin composition of Embodiment 42, wherein the composition comprises 0.0001 to 0.015% by weight *Opuntia tuna* fruit extract. Embodiment 44 is a topical skin composition comprising water, an aqueous extract of *Angelica acutiloba* root, a *Salicornia herbacea* extract, niacinaminde, sodium ascorbyl phosphate and/or ascorbyl glucoside, phenylethyl resorcinol, hydrolyzed pearl extract, glycerin, butylene glycol, caprylic/capric triglyceride, acrylates/C10-30 alkyl acrylate crosspolymer, dimethicone, propandiol, 1,2- hexanediol, isodecyl neopentanoate, petrolatum, PEG-60 glyceryl isostearate, cetyl ethylhexanoate, sorbitol, and ammonium acryloyldimethyltaurate/VP copolymer. Embodiment 45 is a topical skin composition comprising water, an aqueous extract of *Angelica acutiloba* root, a *Salicornia herbacea* extract, niacinaminde, sodium ascorbyl phosphate and/or ascorbyl glucoside, vegetable amnio acids, glycerin, propandiol, butylene glycol, caprylic/capric triglyceride, acrylates/C10-30 alkyl acrylate crosspolymer, dimethicone, 1,2-hexanediol, triethanolamine, disodium ethylenediaminetetraacetic acid, silica, and ammonium acryloyldimethyltaurate/VP crosspolymer. Embodiment 46 is a topical skin composition comprising water, an aqueous extract of *Angelica acutiloba* root, a *Salicornia herbacea* extract, niacinaminde, sodium ascorbyl phosphate and/or ascorbyl glucoside, vegetable amino acids, hydrolyzed pearl extract, glycerin, butylene glycol, caprylic/capric triglyceride, acrylates/C10-30 alkyl acrylate crosspolymer, dimethicone, butylene glycol, 1,2-hexanediol, polyacrylamide, C13-14 isoparaffins, caprylyl glycol, Laureth-7, triethanolamine, octyldodecanol, and dipotassium glycyrrhizate. Embodiment 47 is a topical skin composition comprising water, an aqueous extract of *Angelica acutiloba* root, a *Salicornia herbacea* extract, niacinaminde, sodium ascorbyl phosphate and/or ascorbyl glucoside, vegetable amino acids, hydrolyzed pearl extract, glycerin, butylene glycol, polyethylene glycol (PEG)-75, propandiol, pentylene glycol, caprylic/capric triglyceride, phenoxyethanol, disodium ethylenediaminetetraacetic acid, sodium hylauronate, and triethanolamine. Embodiment 48 is a topical skin composition comprising water, an aqueous extract of *Angelica acutiloba* root, a *Salicornia herbacea* extract, niacinaminde, sodium ascorbyl phosphate and/or ascorbyl glucoside, vegetable amino acids, hydrolyzed pearl extract, glycerin, potassium stearate, dipropylene glycol, sorbitol, potassium myristate, myristic acid, glyceryl stearate SE, PEG-60 glyceryl isostearate, steric acid, sodium methyl cocyl taurate, PEG-32, potassium laurate, glycol stearate, butylene glycol, poly(acrylamide-co-diallyldimethylammonium chloride), and lauric acid. Embodiment 49 is a topical skin composition comprising an effective amount of an aqueous extract of *Angelica acutiloba* root, a *Salicornia herbacea* extract, niacinamide, and a cosmetic vehicle, wherein the composition is capable of conditioning skin or whitening skin or both. Embodiment 50 is the topical skin composition of Embodiment 49, wherein the composition moisturizes skin. Embodiment 51 is a topical skin serum comprising an effective amount of an aqueous extract of *Angelica acutiloba* root, a *Salicornia herbacea* extract, niacinamide, and a cosmetic vehicle wherein the serum is capable of conditioning skin or whitening skin or both. Embodiment 52 is a cream-gel emulsion topical composition comprising an effective amount of an aqueous extract of *Angelica acutiloba* root, a *Salicornia herbacea* extract, niacinamide, and a cosmetic vehicle, wherein the cream-gel emulsion topical composition is capable of conditioning skin or whitening skin or both. Embodiment 53 is a topical skin lotion comprising an effective amount of an aqueous extract of *Angelica acutiloba* root, a *Salicornia herbacea* extract, niacinamide, and a cosmetic vehicle, wherein the lotion is capable of conditioning skin, or whitening or lightening skin or any combination thereof. Embodiment 54 is a topical skin cleanser comprising an effective amount of an aqueous extract of *Angelica acutiloba* root, a *Salicornia herbacea* extract, niacinamide, and a cosmetic vehicle, wherein the cleanser is capable of cleaning skin, conditioning skin, or whitening or any combination thereof.

"Topical application" means to apply or spread a composition onto the surface of lips or keratinous tissue. "Topical skin composition" includes compositions suitable for topical application on skin and/or keratinous tissue. Such compositions are typically dermatologically-acceptable in that they do not have undue toxicity, incompatibility, instability, allergic response, and the like, when applied to skin and/or keratinous tissue. Topical skin care compositions of the present invention can have a selected viscosity to avoid significant dripping or pooling after application to skin and/or keratinous tissue.

"Keratinous tissue" includes keratin-containing layers disposed as the outermost protective covering of mammals and includes, but is not limited to, lips, skin, hair, and nails.

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase, such as a measurable increase of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the terms "comprising," "including," "having," or "containing," or any variations of these terms, in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the phrase "consisting essentially of," a basic and novel property of the compositions and methods of the present invention is the ability of the compositions to both hydrate/moisturize skin and whiten/lighten skin and optionally reduce skin inflammation. The hydration/moisturization aspect can be obtained through *Salicornia herbacea* extract's ability to increase aquaporin 3 (AQP3) production in skin, and the skin whitening and anti-inflammatory aspects can be obtained through *Angelica acutiloba* root extract's ability to reduce tyrosinase activity and reduce IL-6 expression in skin and optionally to reduce oxidative damage in skin caused by free-radicals such as reactive oxygen species.

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

As noted above, the present invention provides a solution to at least some of the problems associated with lack of skin hydration and/or uneven skin color. The solution is premised on the use of a combination of ingredients to promote skin moisturization as well as provide skin lightening or whitening effects to the skin. The combination of ingredients include *Angelica acutiloba* root extract and *Salicornia herbacea* extract and optionally other ingredients such as niacinamide, hydrolyzed pearl extract, vegetable amino acids from the white navy bean, and a chemically modified derivative of ascorbic acid (e.g., sodium ascorbyl phosphate or ascorbyl glucoside)). Notably, and as illustrated in the Examples, this combination of ingredients can have a dual skin hydration and skin lightening effect on skin, and it can also have an anti-inflammatory effect on skin. Cosmetic formulations were also identified that allows for the combination of ingredients to stably co-exist and retain their efficacy. Without wishing to be bound by theory, it is believed that the cosmetic formulations help reduce or avoid cross-reactivity between the aforementioned ingredients, thereby allowing for their co-existence in a single formulation while retaining their efficacy.

These and other non-limiting aspects of the present invention are described in the following sections.

A. Combination of Active Ingredients

*Angelica acutiloba* is found predominately in Japan (e.g., Hokkaido). The roots from this plant can be extracted by using water as the extracting solvent to obtain an *Angelica acutiloba* root extract of the present invention. The extract can be in liquid form and in preferred instances can further include butylene glycol. Such an extract is commercially available under the trade name Angelys, which is sold by Barnet Products Corporation (U.S.A.). Other extracting solvents such as alcohols, glycols, alcohol/aqueous mixtures, or alcohol/gycol mixtures can be used. It was discovered in the context of the present invention that this extract can reduce tyrosinase activity in skin, which can result in decreased melanin production, and ultimately whiten or lighten skin. It was also discovered that this extract has anti-oxidative properties against free radicals or reactive oxygen species. It was further discovered that this extract has the ability to reduce IL-6 activity in skin, which can be beneficial for skin given that IL-6 is part of the inflammatory pathway.

*Salicornia herbacea* is found predominately in the coastal regions of North America, Europe, South Africa, and South Asia. An extract of *Salicornia herbacea* can be produced through a supercritical extraction process using carbon dioxide ($CO_2$). The resulting extract can be lipophilic and can be in liquid form. The liquid extract can also include caprylic/capric triglycerides. The whole plant or individual parts of the plant (roots, stems, leaves, flowers, seeds, etc.) can be used to make the extract. In certain instances, the whole plant is used. Such an extract is commercially available under the trade name Saliporine 8, which is sold by Barnet Products Corporation (U.S.A.). It was discovered in the context of the present invention that *Salicornia herbacea* extract has the ability to increase aquaporin 3 (AQP3) production in skin, which can be beneficial in hydrating or moisturizing skin, as AQP3 can act as a membrane transporter of water and glycerol expressed in plasma membranes in the basal layer of keratinocytes of the epidermis.

Hydrolyzed pearl extract is an extract of alkaline hydrolyzed black pearl powder. The pearl powder is a marine-based mineral that can be formed from the black lip oyster (*Pinctada margaritifera*), which can be found around the islands of French Polynesia, around Tahiti. The extract can be produced by cultivating the pearls from the black lip oyster and crushing the pearls to form a powder. The powder can then be subjected to an alkaline hydrolysis process followed by a neutralization step and then solubilized in a glycerin/water mixture. Such an extract is commercially available under the trade name Crodarom® Black Pearl, which is sold by Crodarom S.A.S. (France). It was discovered in the context of the present invention that hydrolyzed pearl extract can reduce melanin production in melanocytes and can also reduce the activity of tyrosinase, both of which can be beneficial to treating melanogenesis or hyperpigmentation in skin. It was also discovered that this extract can reduce MMP-9 activity in skin, which can be beneficial for treating fine lines or wrinkles or sagging or non-elastic skin, as MMP-9 enzymes are extracellular proteases that can degrade important skin structural proteins such as collagen VII, fibronectins, and laminin.

Vegetable amino acids of the present invention are obtained from the navy (haricot)-bean (*Phaseolus vulgaris*) ("navy bean"). The navy bean is a small oval-shaped bean that has a white appearance. It is produced worldwide from North America to Europe to Africa to Asia. The navy bean is different from green beans, anasazi beans, black beans, cranberry or borlotti beans, chickpeas, lentil beans, pink beans, pinto beans, red kidney beans, shell beans, and yellow beans. Vegetable amino acids from the navy bean have been discovered to significantly improve the brightness of the skin. They have also been shown to improve the overall evenness of skin tone and reduce the visible contrast of dark spots on the skin as it targets melanin production. The vegetable amino acids can be produced by contacting navy bean powder (dried navy beans that have been crushed) with water as an extracting solvent. The resulting extract is a liquid aqueous extract of navy bean having amino acids from the navy bean. Such an extract is commercially available from Carrubba Inc. (Milford, Conn. USA). Also, dried navy bean powder, which can be used to produce the extract, can be obtained from InfraReady Products Ltd. (CANADA). It was discovered in the context of the present invention that vegetable amino acids from navy bean can be used to reduce melanin production in melanocytes and reduce tyrosinase activity, which can be beneficial to treating melanogenesis or hyperpigmentation in skin.

Niacinamide (also known as vitamin $B_3$) is an organic compound having the following chemical structure:

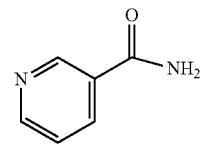

Niacinamide is commercially available from a variety of sources. A non-limiting example of a commercial supplier of niacinamide is DSM (Switzerland) under the trade name Niacinamide PC. It was discovered in the context of the present invention that niacinamide can be used to reduce melanin production in melanocytes, which can be beneficial to treating melanogenesis or hyperpigmentation in skin.

Two different types of ascorbic acid (vitamin C) derivatives can be used in the context of the present invention. One is sodium ascorbyl phosphate, which has the following chemical structure:

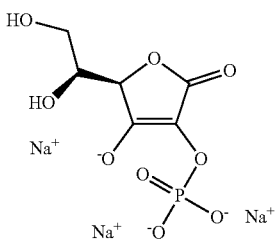

Sodium ascorbyl phosphate is commercially available from a variety of sources. A non-limiting example of a commercial supplier of sodium ascorbyl phosphate is DSM (Switzerland) STAY-C® 50. Alternatively, or additionally, ascorbyl glucoside can be used as the ascorbic acid derivative. The ascorbyl glucoside can be 1-ascorbic acid 2-glucoside, which can have the following structure:

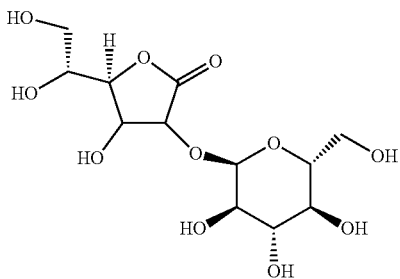 [SMILES: O=C1O[C@H]([C@H](O)CO)C(O)C1O[C@H]1O[C@H](CO)[C@@H](O)[C@H](O)[C@H]1O]

In a particular instance, the ascorbyl glucoside can be purchased from Hayashibara Company (Japan) under the trade name AA2G™. It was discovered in the context of the present invention that sodium ascorbyl phosphate has the ability to reduce melanin production in melanocytes and reduce tyrosinase activity, which can be beneficial to treating melanogenesis or hyperpigmentation in skin. It was also discovered that sodium ascorbyl phosphate has anti-oxidative properties and can act as an antioxidant to free radicals or reactive oxygen species. Still further, it was discovered that sodium ascorbyl phosphate has the ability to increase collagen-1 expression, which can be beneficial in reducing the appearance of fine lines or wrinkles or reducing the appearance of sagging or non-elastic skin. Also, sodium ascorbyl phosphate was discovered to have the ability to increase lysyl oxidase in skin, which can be beneficial in reducing the appearance of fine lines or wrinkles or reducing the appearance of sagging or non-elastic skin by increasing cross-linking of elastins and collagens, thereby creating a more structurally sound matrix of supportive proteins in the skin. Sodium ascorbyl phosphate was also found to have the ability to reduce both TNF-alpha and lipoxygenase activity in skin, which can be beneficial in treating inflamed skin.

The extracts described herein can be extracts made through extraction methods known in the art and combinations thereof. Non-limiting examples of extraction methods include the use of liquid-liquid extraction, solid phase extraction, aqueous extraction, ethyl acetate, alcohol, acetone, oil, supercritical carbon dioxide, heat, pressure, pressure drop extraction, ultrasonic extraction, etc. Extracts can be a liquid, solid, dried liquid, re-suspended solid, etc. The extracting solvent used to obtain the extract from the plant can be water, alcohol, a glycol, or any combination thereof. The extracting solvent contacts the whole plant or plant part (root, stem, leaves, flowers, buds, seeds, etc.) and extracts compounds and materials that are soluble within the extracting solvent. If a hydrophilic extracting solvent such as water is used, then the resulting extract can be characterized as a hydrophilic extract. If a hydrophobic extracting solvent such as oil is used, then the resulting extract can be characterized as a hydrophobic extract. The extracting solvent can dictate the type of extract that is produced based on the solubility of the plant compounds and materials in the extracting solvent.

B. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

C. Vehicles

The compositions of the present invention can include or be incorporated into all types of vehicles and carriers. The vehicle or carrier can be a pharmaceutically or dermatologically acceptable vehicle or carrier. Non-limiting examples of vehicles or carriers include water, glycerin, alcohol, oil, a silicon containing compound, a silicone compound, and wax. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

D. Structure

The compositions of the present invention can be structured or formulated into a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), cleansers, toners, serums, gels, masks, scrubs, body butters, peels, and ointments. Variations and other structures will be apparent to the skilled artisan and are appropriate for use in the present invention. Lotions and creams are generally structured as water-in-oil emulsions. Toners, serums, and cleansers can be aqueous solutions, gels, or oil-in-water emulsions. One difference between toners, serums, and cleansers when compared with lotions and creams is that the former tend to be less viscose than the latter.

E. Additional Ingredients

In addition to the combination of ingredients described throughout the specification, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrance agents (artificial and natural; e.g., gluconic acid, phenoxyethanol, and triethanolamine), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), flavoring agents/aroma agents (e.g., *Stevia rebaudiana* (sweetleaf) extract, and menthol), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., *Aloe vera*, chamomile, cucumber extract, *Ginkgo biloba*, ginseng, and rosemary), anti-microbial agents, antioxidants (e.g., BHT and tocopherol), chelating agents (e.g., disodium EDTA and tetrasodium EDTA), preservatives (e.g., potassium benzoate, sorbic acid, potassium sorbate, methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, saccharide isomerate, and mannitol), exfoliants, waterproofing agents (e.g., magnesium/aluminum hydroxide stearate), skin conditioning agents (e.g., *Aloe* extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

a. UV Absorption and/or Reflecting Agents

UV absorption and/or reflecting agents that can be used in combination with the compositions of the present invention include chemical and physical sunblocks. Non-limiting examples of chemical sunblocks that can be used include para-aminobenzoic acid (PABA), PABA esters (e.g., glyceryl PABA, amyldimethyl PABA and octyldimethyl PABA), butyl PABA, ethyl PABA, ethyl dihydroxypropyl PABA, benzophenones (e.g., oxybenzone, sulisobenzone, benzophenone, and benzophenone-1 through 12), cinnamates (e.g., octyl methoxycinnamate (octinoxate), isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (e.g., homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, saccharide isomerate, sodium glucuronate, sodium PCA, sorbitol, sucrose, trehalose, urea, and xylitol.

Other examples include acetylated lanolin, acetylated lanolin alcohol, alanine, algae extract, *Aloe barbadensis*, *Aloe barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, matricaria (*Chamomilla recutita*) oil, methyl glucose sesquistearate, methylsilanol PCA, mineral oil, mink oil, *Mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (see, for example, U.S. Pat. Nos. 5,011,681; 4,421,769; and 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Exfoliating Agent

Exfoliating agents include ingredients that remove dead skin cells on the skin's outer surface. These agents may act through mechanical, chemical, and/or other means. Non-limiting examples of mechanical exfoliating agents include abrasives such as pumice, silica, cloth, paper, shells, beads, solid crystals, solid polymers, etc. Non-limiting examples of chemical exfoliating agents include acids and enzyme exfoliants. Acids that can be used as exfoliating agents include, but are not limited to, glycolic acid, lactic acid, citric acid, alpha hydroxy acids, beta hydroxy acids, etc. Other exfoliating agents known to those of skill in the art are also contemplated as being useful within the context of the present invention.

h. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, *Macadamia* nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *Eucalyptus* oil, fennel oil, sea fennel oil, frankincense oil, *Geranium* oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang. Other essential oils known to those of skill in the art are also contemplated as being useful within the context of the present invention.

i. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/VP copolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see, for example, U.S. Pat. Nos. 5,087,445; 4,509,949; 2,798,053; and CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol® 900 series from Lubrizol Advanced Materials, Inc.). Other examples, include acrylates/C10-C13 alkyl acrylate crosspolymer (e.g., Pemulen™ TR-1, Carbopol®1342 from Lubrizol).

Non-limiting examples of cross-linked polyacrylate polymers include cationic and nonionic polymers. Non-limiting examples are described in U.S. Pat. Nos. 5,100,660; 4,849,484; 4,835,206; 4,628,078; and 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention can include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

j. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, potassium benzoate, potassium sorbate, thimerosal or combinations thereof 2. Pharmaceutical Ingredients Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, anti seborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The skin active ingredients in Table 1 were used to procure the in vitro data in Example 1 and the formulations described in Examples 2 to 6.

TABLE 1

Skin Active Ingredients

Niacinamide was supplied by DSM under the trade name Niacinamide.
Aqueous extract of *Angelica acutiloba* root was supplied by Barnet under the trade name Angelys.
Extract of *Salicornia herbacea* was supplied by Barnet under the tradename Saliporine-8.
Hydrolyzed pearl extract was supplied by glycerin/water solution by Crodarom S.A.S. (France) under the trade name Crodarom ® Black Pearl.
Sodium ascorbyl phosphate is a vitamin C derivate and was supplied by DSM under the trade name STAY-C ® 50.
Ascorbyl glucoside is a Vitamin C derivate and was supplied by Hayashibara under the trade name AA2G ™.
Aqueous vegetable amino acids (navy bean extract) were supplied by Carrubba under the trade name Vegetable Amino Acids.

Example 1

In Vitro Data

B16 Pigmentation Assay:

Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, were cultivated in standard DMEM growth medium with 10% fetal bovine serum (Mediatech) at 37° C. in 10% $CO_2$ and then treated with the ingredients in the amounts indicated in Table 2 for 6 days. Following incubation, melanin secretion was measured by absorbance at 405 nm and cellular viability is quantified.

TABLE 2

(B16 melanogenesis data)

| Ingredients | Concentration | % of Inhibition |
|---|---|---|
| Black Pearl | 1% | 16% |
| Vegetable Amino Acids | 1% | 30% |
| Niacinamide | 1% | 30% |

Mushroom Tyrosinase Activity Assay:

In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) was incubated with its substrate L-Dopa (Fisher) in the presence of each of the ingredients in the amounts indicated in Table 3. Pigment formation was evaluated by colorimetric plate reading at 490 nm. The percent inhibition of mushroom tyrosinase activity was calculated compared to non-treated controls to determine the ability of tested ingredients to inhibit the activity of purified enzyme.

TABLE 3

(Mushroom Tyrosinase Inhibition)

| Ingredients | Concentration* | % of Inhibition |
|---|---|---|
| Black Pearl | 0.75% | 61% |
| Angelys | 1% | 66% |
| Stay C 50 | 1% | 26% |
| Vegetable Amino Acids | 1% | 40% |

Aquaporin 3 mRNA Expression:

1% of Saliporine-8 was applied to the surface of a reconstituted human epidermis. The effect of Saliporine on Aquaporin 3 (AQP3) was measured by gene expression (mRNA) by RT-PCR and protein expression was quantified by western blotting. It was discovered that 1% Saliporine-8 stimulated the expression of Aquaporin 3 mRNA by 30%, as evidenced in Table 4. This can be beneficial in treating dry skin or skin that is in need of increased moisturization. In particular, a lack of sufficient AQP3 expression in keratinocytes can present as an epidermal phenotype characterized by dry skin, decreased skin elasticity, and delayed barrier repair to wound healing. This is believed to be due to AQP3's function as a membrane transporter of water and glycerol expressed in plasma membranes in the basal layer of keratinocytes of the epidermis.

TABLE 4

(Aquaporin 3 Protein Expression)

| Ingredients | Concentration | % of expression |
|---|---|---|
| Saliporine-8 | 1% | 30% |

Antioxidant (AO) Assay:

An in vitro bioassay that measures the total anti-oxidant capacity of the ingredients in the amounts indicated in Table 5 was used. The assay relies on the ability of antioxidants in the sample to inhibit the oxidation of ABTS® (2,2'-azino-di-[3-ethylbenzthiazoline sulphonate]) to ABTS®+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation was compared with that of Trolox, a water-soluble tocopherol analogue, and was quantified as molar Trolox equivalents. Anti-Oxidant capacity kit #709001 from Cayman Chemical (Ann Arbor, Mich. USA) was used to measure the total anti-oxidant capacity of each of the ingredients in the amounts indicated in Table 5.

TABLE 5

(Anti-oxidant capacity)

| Ingredients | Concentration | % of Inhibition |
|---|---|---|
| Angelys | 1% | 49% |
| Stay C 50 | 1% | 97% |

Collagen Stimulation Assay:

Collagen is an extracellular matrix protein critical for skin structure. Increased synthesis of collagen helps improve skin firmness and elasticity. This bioassay was used to examine effects on the production of procollagen peptide (a precursor to collagen) by human epidermal fibroblasts. The endpoint of this assay was a spectrophotometric measurement that reflects the presence of procollagen peptide and cellular viability. The assay employed the quantitative sandwich enzyme immunoassay technique whereby a monoclonal antibody specific for procollagen peptide was pre-coated onto a microplate. Standards and samples were pipetted into the wells and any procollagen peptide present was bound by the immobilized antibody. After washing away any unbound substances, an enzyme-linked polyclonal antibody specific for procollagen peptide was added to the wells. Following a wash to remove any unbound antibody-enzyme reagent, a substrate solution was added to the wells and color was developed in proportion to the amount of procollagen peptide bound in the initial step. Color development was stopped and the intensity of the color at 450 nm was measured using a microplate reader.

For generation of samples and controls, subconfluent normal human adult epidermal fibroblasts (Cascade Biologics) were cultivated in standard DMEM growth medium with 10% fetal bovine serum (Mediatech) at 37° C. in 10% $CO_2$. The cells were treated with each of the tested ingredients and controls for 3 days. Following incubation, cell culture medium was collected and the amount of Type I procollagen peptide secretion was quantified using the sandwich enzyme linked immuno-sorbant assay (ELISA) from Takara (#MK101) as explained above. This assay was used to determine the effectiveness of the ingredient in the amounts indicated in Table 6 to increase collagen I expression in human adult epidermal fibroblasts.

TABLE 6

(Collagen 1 Expression)

| Ingredients | Concentration | % of expression |
|---|---|---|
| Stay C 50 | 1% | 36% |

Matrix Metalloproteinase Enzyme Activity (MMP) Assay:

An in vitro matrix metalloprotease (MMP) inhibition assay was used to determine the effectiveness of the ingredients in the amount indicated in Table 7 to inhibit MMP expression in skin. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), these assays are designed to measure protease activity of MMPs using a thiopeptide as a chromogenic substrate (Ac-PLG-[2-mercapto-4-methyl-pentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\varepsilon$=13,600 M-1 cm-1 at pH 6.0 and above 7).

TABLE 7

(MMP Inhibition)

| Ingredients | Concentration | % of inhibition |
|---|---|---|
| Black Pearl | 1% | 35% |

Lysyl Oxidase Assay:

A lysyl oxidase assay was performed on skin cells (e.g., epidermal keratinocytes, fibroblasts, and/or dermal endothelial cells) to determine the ability of the ingredient listed in Table 8 to stimulate expression of lysyl oxidase in skin. Lysyl oxidase can catalyze crosslinking of elastin and collagens, thereby providing for a more structurally rigid matrix for skin. By increasing expression of lysyl oxidase, increased cross-linking of elastin and collagens can occur, which can be beneficial in reducing the appearance of fine lines, wrinkles, sagging skin, and/or non-elastic skin.

TABLE 8

(Lysyl Oxidase)

| Ingredients | Concentration | % of expression |
|---|---|---|
| Stay C 50 | 1% | 500% |

Tumor Necrosis Factor Alpha (TNF-α) Assay:

The prototype ligand of the TNF superfamily, TNF-α, is a pleiotropic cytokine that plays a central role in inflammation. Increase in its expression is associated with an up regulation in pro-inflammatory activity. This bioassay was used to analyze the effect of the ingredients in the amounts listed in Table 9 on the production of TNF-α by human epidermal keratinocytes. The endpoint of this assay was a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples were pipetted into the wells and any TNF-α present is bound by the immobilized antibody. After washing away any unbound substances, an enzyme-linked polyclonal antibody specific for TNF-α is added to the wells. Following a wash to remove any unbound antibody-enzyme reagent, a substrate solution is added to the wells and color develops in proportion to the amount of TNF-α bound in the initial step using a microplate reader for detection at 450 nm. The color development was stopped and the intensity of the color was measured. Subconfluent normal human adult keratinocytes (Cascade Biologics) cultivated in EpiLife standard growth medium (Cascade Biologics) at 37° C. in 5% $CO_2$, were treated with phorbol 12-myristate 13-acetate (PMA, 10 ng/ml, Sigma Chemical, #P1585-1MG) and the ingredients in the amounts listed in Table 9 for 6 hours. PMA has been shown to cause a dramatic increase in TNF-α secretion which peaks at 6 hours after treatment. Following incubation, cell culture medium was collected and the amount of TNF-α secretion quantified using a sandwich enzyme linked immuno-sorbant assay (ELISA) from R&D Systems (#DTA00C).

TABLE 9

(TNF-α Expression)

| Ingredients | Concentration | % of expression |
|---|---|---|
| Stay C 50 | 1% | 85% |

IL-6 Assay:

An interleukin-6 (IL-6) assay was performed on skin cells (e.g., epidermal keratinocytes, fibroblasts, and/or dermal endothelial cells) to determine the ability of the ingredient listed in Table 8 to inhibit IL-6 activity in skin. IL-6 is known to induce inflammation in skin. Reducing IL-6 expression in skin would lead to reduced skin inflammation.

TABLE 10

(IL-6 Inhibition Assay)

| Ingredients | Concentration | % of inhibition (TNF-alpha) |
|---|---|---|
| Angelys | 1% | 79% |

General Procedure

The formulations described in the following Tables can each be prepared by mixing the ingredients in a beaker under heat 70-75° C. until homogenous. Subsequently, the formulations can be cooled to standing room temperature (20-25° C.). Further, and if desired, additional ingredients can be added, for example, to modify the rheological properties of the composition or ingredients that provide benefits to skin. In all the procedures, excipients can be added, for example, to modify the rheological properties of the composition, modify the pH, or act as a preservative.

Example 2

Lotion Formulations

Tables 11, 12, and 13 represent skin lotion formulations of the present invention, which is structured as an oil-in-water emulsion. The formulations exhibited the ability to reduce skin pigmentation, which can even skin tone and reduce the appearance of hyperpigmented or melasmic skin such as sun spots, age spots, freckles. Further, the formulation also exhibited the ability to increase skin hydration.

TABLE 11

| Ingredient | % Concentration (by weight) |
|---|---|
| Water | 74.29 |
| Glycerin | 4.67 |
| Hydrogenated polydecene | 3.70 |
| Dimethicone | 2.90 |
| Isodecyl neopentanoate | 2.15 |
| Niacinamide | 2.00 |
| Butylene glycol | 1.98 |
| Petrolatum | 1.75 |
| PEG-60 glyceryl isosterate | 1.50 |
| Cetyl ethylhexanoate | 0.90 |
| Ammonium acryloyldimethyltaurate/VP copolymer | 0.60 |
| Sorbitol | 0.56 |
| Phenoxyethanol | 0.48 |
| Caprylyl glycol | 0.37 |
| Vegetable amino acids | 0.30 |
| Acrylates/C10-30 alkyl acrylate crosspolymer | 0.30 |
| Sodium ascorbyl phosphate | 0.25 |
| Caprylic/capric triglyceride | 0.24 |
| Behenyl alcohol | 0.20 |
| Potassium hydroxide | 0.14 |
| Triethyl citrate | 0.13 |
| Microcrystalline wax (cera microcristallina) | 0.10 |
| Dipotassium glycyrrhizate | 0.10 |
| Disodium EDTA | 0.10 |
| Hydroxypropyl cyclodextrin | 0.07 |
| *Angelica acutiloba* root extract | 0.04 |
| Hydrolyzed pearl extract | 0.03 |
| *Salicornia herbacea* extract | 0.01 |
| Iodopropynyl butylcarbamate | 0.01 |
| Potassium benzoate | 0.01 |
| *Opuntia tuna* fruit extract | 0.0005 |
| Excipients* | q.s. |

TABLE 12

| Ingredient | % Concentration (by weight) |
|---|---|
| Water | 73 |
| Hydrogenated polydecene | 4 |
| Glycerin | 3 |
| Dimethicone | 3 |
| Isodecyl neopentanoate | 2 |
| Niacinamide | 2 |
| Butylene glycol | 2 |
| Petrolatum | 2 |
| Propanediol | 2 |
| PEG-60 glyceryl isostearate | 1 |
| Cetyl ethylhexanoate | 0.9 |
| Hydroxyacetophenone | 0.8 |
| Sorbitol | 0.6 |
| 1,2-hexanediol | 0.5 |
| Ammonium acryloyldimethyltaurate/VP copolymer | 0.5 |
| Caprylic/capric triglyceride | 0.3 |
| Acrylates/C10-30 alkyl acrylate crosspolymer | 0.3 |
| Sodium ascorbyl phosphate and/or ascorbyl glucoside | 0.3 |
| Behenyl alcohol | 0.2 |
| Potassium hydroxide | 0.1 |
| Dipotassium glycyrrhizate | 0.1 |
| Disodium EDTA | 0.1 |
| Microcrystalline wax | 0.1 |
| Pentylene glycol | 0.1 |
| Phenylethyl resorcinol | 0.04 |
| *Angelica acutiloba* root extract | 0.04 |
| Hydrolyzed pearl extract | 0.03 |
| *Salicornia herbacea* extract | 0.009 |
| Vegetable amino acids (Navy bean) (optional) | 0.3 |
| *Opuntia tuna* fruit extract (optional) | 0.0005 |
| Excipients* | q.s. |

TABLE 13

| Ingredient | % Concentration (by weight) |
|---|---|
| Water | 71 |
| Hydrogenated polydecene | 4 |
| Glycerin | 3 |
| Propanediol | 3 |
| Dimethicone | 3 |
| Isodecyl neopentanoate | 2 |
| Niacinamide | 2 |
| Butylene glycol | 2 |
| Petrolatum | 2 |
| PEG-60 glyceryl isostearate | 1 |

TABLE 13-continued

| Ingredient | % Concentration (by weight) |
| --- | --- |
| 1,2-hexanediol | 1 |
| Cetyl ethylhexanoate | 0.9 |
| Sorbitol | 0.6 |
| Ammonium acryloyldimethyltaurate/VP copolymer | 0.6 |
| Hydroxyacetophenone | 0.5 |
| Caprylic/capric triglyceride | 0.3 |
| Acrylates/C10-30 alkyl acrylate crosspolymer | 0.3 |
| Sodium ascorbyl phosphate and/or ascorbyl glucoside | 0.3 |
| Behenyl alcohol | 0.2 |
| Potassium hydroxide | 0.1 |
| Dipotassium glycyrrhizate | 0.1 |
| Disodium EDTA | 0.1 |
| Microcrystalline wax | 0.1 |
| Pentylene glycol | 0.1 |
| Phenylethyl resorcinol | 0.05 |
| *Angelica acutiloba* root extract | 0.04 |
| Hydrolyzed pearl extract (optional) | 0.03 |
| *Salicornia herbacea* extract | 0.009 |
| Vegetable amino acids (Navy bean) (optional) | 0.3 |
| *Opuntia tuna* fruit extract (optional) | 0.0005 |
| Excipients* | q.s. |

*Excipients can be added to modify the rheological properties of the formulation or to provide additional skin care benefits or to provide additional preservatives. Such excipients can include Polyquaternium-51, sorbic acid, potassium sorbate, citric acid, cyclohexasiloxane, botanical plant extracts and/or oils, tocopherol, sodium benzoate, and/or botanical extracts and/or oils. If excipients are added, then they can be added such that the formulation includes 100 wt. % of ingredients. If excipients are not added, then the amount of water can be adjusted accordingly such that the formulation includes 100 wt. % of ingredients.

It was discovered that the combination of propanediol, 1,2-hexanediol, hydroxyacetonphenone, pentylene glycol, phenylethyl resorcinol, and bisabolol led to some skin irritation issues. When these ingredients were removed and replaced with vegetable amino acids, hydroxypropyl cyclodextrin, iodopropynyl butylcarbamate, and potassium benzoate, the skin irritation issues were ameliorated.

Example 3

Serum Formulation

Table 14 represents a serum formulation of the present invention. This formulation exhibited the ability to reduce skin pigmentation, which can even skin tone and reduce the appearance of hyperpigmented or melasmic skin such as sun spots, age spots, freckles. Further, the formulations also exhibited the ability to increase skin hydration.

TABLE 14

| Ingredient | % Concentration (by weight) |
| --- | --- |
| Water | 75.55 |
| Propanediol | 6.00 |
| Dimethicone | 5.00 |
| Glycerin | 3.7 |
| Niacinamide | 2.00 |
| Silica | 2.00 |
| Ascorbyl glucoside | 1.05 |
| Triethanolamine | 1.01 |
| Caprylic/capric triglyceride | 0.97 |
| Butylene glycol | 0.48 |
| Ammonium acryloyldimethyltaurate/VP copolymer | 0.40 |
| Acrylates/C10-30 Alkyl acrylate crosspolymer | 0.30 |
| Polysorbate 20 | 0.30 |
| Vegetable amino acids | 0.30 |
| Capryl glycol | 0.27 |
| 1,2-hexanediol | 0.24 |
| Disodium EDTA | 0.10 |
| Xanthan gum | 0.10 |
| *Angelica acutiloba* root extract | 0.04 |

TABLE 14-continued

| Ingredient | % Concentration (by weight) |
| --- | --- |
| *Salicornia herbacea* extract | 0.04 |
| Hydrolyzed pearl extract | 0.03 |
| *Opuntia tuna* fruit extract (optional) | 0.0005 |
| Excipients | q.s. |

*Excipients can be added to modify the rheological properties of the formulation or to provide additional skin care benefits or to provide additional preservatives. Such excipients can include hydroxypropyl cyclodextrin, triethyl citrate, citric acid, potassium sorbate, iodopropynyl butylcarbamate, potassium benzoate, sorbic acid, sodium benzoate, and/or botanical plant extracts and/or oils. If excipients are added, then they can be added such that the formulation includes 100 wt. % of ingredients. If excipients are not added, then the amount of water can be adjusted accordingly such that the formulation includes 100 wt. % of ingredients.

Example 4

Toner Formulation

Table 15 represents a Toner formulation of the present invention, which is structured as an aqueous solution. This formulation exhibited the ability to reduce skin pigmentation, which can even skin tone and reduce the appearance of hyperpigmented or melasmic skin such as sun spots, age spots, freckles. Further, the formulations also exhibited the ability to increase skin hydration.

TABLE 15

| Ingredient | % Concentration (by weight) |
| --- | --- |
| Water | 84.10 |
| PEG-75 | 3.00 |
| Butylene glycol | 2.05 |
| Propanediol | 2.00 |
| Glycerin | 1.69 |
| Trideceth-9 | 1.11 |
| Ceteareth-33 | 1.00 |
| Niacinamide | 1.00 |
| PEG-40 hydrogenated castor oil | 0.82 |
| Betaine | 0.50 |
| Pentylene glycol | 0.50 |
| Phenoxyethanol | 0.45 |
| Vegetable amino acids | 0.30 |
| Caprylic/capric triglyceride | 0.24 |
| Triethanolamine | 0.24 |
| Coceth-7 | 0.20 |
| PPG-1-PEG-9 Lauryl glycol ether | 0.18 |
| Disodium EDTA | 0.10 |
| Dipotassium glycyrrhizate | 0.10 |
| Sodium ascorbyl phosphate and/or ascorbyl glucoside | 0.10 |
| Hydrolyzed pearl extract | 0.03 |
| *Salicornia herbacea* extract | 0.009 |
| *Angelica acutiloba* root extract | 0.004 |
| *Opuntia tuna* fruit extract (optional) | 0.0005 |
| Excipients | q.s. |

*Excipients can be added to modify the rheological properties of the formulation or to provide additional skin care benefits or to provide additional preservatives. Such excipients can include hydroxylpropyl cyclodextrin, carbomer, polysorbate 20, ethylhexylglycerin, triethyl citrate, potassium sorbate, iodopropynyl butylcarbamate, citric acid, potassium benzoate, simethicone, sodium hyaluronate, sorbic acid, sodium benzoate, cyclohexasiloxane, tocopherol, and/or botanical plant extracts and/or oils. If excipients are added, then they can be added such that the formulation includes 100 wt. % of ingredients. If excipients are not added, then the amount of water can be adjusted accordingly such that the formulation includes 100 wt. % of ingredients.

Example 5

Eye Cream

Table 16 represents an eye cream of the present invention, which is structured as an oil-in-water emulsion. This formulation exhibited the ability to reduce skin pigmentation, which can even skin tone and reduce the appearance of hyperpigmented or melasmic skin such as sun spots, age spots, freckles. Further, the formulations also exhibited the ability to increase skin hydration.

TABLE 16

| Ingredient | % Concentration (by weight) |
| --- | --- |
| Water | 76.13 |
| Glycerin | 9.62 |
| Dimethicone | 4.56 |
| Niacinamide | 2.00 |
| Silica | 1.00 |
| Triethanolamine | 0.99 |
| Octadodecanol | 0.75 |
| Polyacrylamide | 0.70 |
| Dimethiconol | 0.60 |
| Ascorbyl glucoside | 0.50 |
| Acrylates/C10-30 alkyl acrylate crosspolymer | 0.50 |
| C13-14 isoparaffins | 0.35 |
| Vegetable amino acids | 0.30 |
| Caprylyl glycol | 0.27 |
| Mica | 0.26 |
| Caprylic/capric triglyceride | 0.24 |
| Butylene glycol | 0.24 |
| 1,2-Hexanediol | 0.24 |
| Titanium dioxide | 0.21 |
| Dipotassium glycyrrhizate | 0.10 |
| Disodium EDTA | 0.10 |
| Hydrolyzed pearl extract | 0.03 |
| *Angelica acutiloba* root extract | 0.02 |
| *Salicornia herbacea* extract | 0.01 |
| Excipients | q.s. |

*Excipients can be added to modify the rheological properties of the formulation or to provide additional skin care benefits or to provide additional preservatives. Such excipients can include laureth-7, hydroxypropyl cyclodextrin, dimethicone crosspolymer, cyclopentasilozane, cyclohexasiloxane, potassium sorbate, iodopropynyl butylcarbamate, citric acid, potassium benzoate, sorbic acid, and/or botanical plant extracts and/or oils. If excipients are added, then they can be added such that the formulation includes 100 wt. % of ingredients. If excipients are not added, then the amount of water can be adjusted accordingly such that the formulation includes 100 wt. % of ingredients.

Example 6

Skin Cleanser Formulation

Table 17 represents a skin cleanser formulation of the present invention. This formulation exhibited the ability to reduce skin pigmentation, which can even skin tone and reduce the appearance of hyperpigmented or melasmic skin such as sun spots, age spots, freckles. Further, the formulations also exhibited the ability to increase skin hydration.

TABLE 17

| Ingredient | % Concentration (by weight) |
| --- | --- |
| Water | 29.77 |
| Glycerin | 19.98 |
| Potassium stearate | 17.01 |
| Dipropylene glycol | 6.75 |
| Sorbitol | 4.73 |
| Potassium myristate | 3.15 |
| Myristic Acid | 3.00 |
| Glyceryl stearate SE | 2.50 |
| PEG-60 glyceryl isostearate | 2.50 |
| Stearic acid | 2.10 |
| Sodium methyl cocyl taurate | 1.72 |
| PEG-32 | 1.35 |
| Potassium laurate | 1.24 |
| Glycol stearate | 1.00 |
| PEG-6 | 0.90 |
| Butylene glycol | 0.55 |
| Polyquaternium-7 | 0.50 |
| Lauric acid | 0.33 |
| Sodium chloride | 0.28 |

TABLE 17-continued

| Ingredient | % Concentration (by weight) |
| --- | --- |
| PEG-4 laurate | 0.16 |
| Triethyl citrate | 0.13 |
| Niacinamide | 0.10 |
| Sodium ascorbyl phosphate | 0.10 |
| Caprylic/capric triglyceride | 0.10 |
| Vegetable amino acids | 0.01 |
| *Angelica acutiloba* root extract | 0.004 |
| *Salicornia herbacea* extract | 0.004 |
| Hydrolyzed pearl extract | 0.003 |
| Excipients | q.s. |

*Excipients can be added to modify the rheological properties of the formulation or to provide additional skin care benefits or to provide additional preservatives. Such excipients can include iodopropynyl butylcarbamate, potassium sorbate, tocopherol, citric acid, potassium benzoate, sorbic acid, and/or botanical plant extracts and/or oils. If excipients are added, then they can be added such that the formulation includes 100 wt. % of ingredients. If excipients are not added, then the amount of water can be adjusted accordingly such that the formulation includes 100 wt. % of ingredients.

Example 7

Additional Assays

Assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

Elastin Stimulation Assay:

Elastin is a connective tissue protein that helps skin resume shape after stretching or contracting. Elastin is also an important load-bearing protein used in places where mechanical energy is required to be stored. Elastin is made by linking many soluble tropoelastin protein molecules, in a reaction catalyzed by lysyl oxidase. Elastin secretion and elastin fibers were monitored in cultured human fibroblasts by a direct ELISA sandwich method and analyzed using the Meso Scale Discovery system SECTOR 2400 Imaging system.

Laminin and Fibronectin Stimulation Assay:

Laminin and fibronectin are major proteins in the dermal-epidermal junction (DEJ) (also referred to as the basement membrane). The DEJ is located between the dermis and the epidermis interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin and fibronectin are two structural glycoproteins located in the DEJ. Considered the glue that holds the cells together, laminin and fibronectin are secreted by dermal fibroblasts to help facilitate intra- and inter-cellular adhesion of the epidermal calls to the DEJ.

Laminin and fibronectin secretion were monitored by quantifying laminin and fibronectin in cell supernatants of cultured human fibroblasts treated for 3 days with culture medium with or without 1.0% final concentration of the test ingredient(s). Following incubation, laminin and fibronectin content was measured using immunofluorescent antibodies directed against each protein in an enzyme linked immunosorbant assay (ELISA).

ORAC Assay:

Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. Antioxidant activity indicates a capability to reduce oxidizing agents (oxidants). This assay quantifies the degree and length of time it takes to inhibit the action of an oxidizing agent, such as oxygen radicals, that are known to cause damage to cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; and commercially available kits such as Zen-Bio ORAC Anti-oxidant Assay kit (#AOX-2)). The Zen-Bio ORAC Anti-oxidant Assay kit measures the loss of fluorescein fluorescence over time due to the peroxyl-radical formation by the breakdown of AAPH (2,2'-axobis-2-methyl propanimidamide, dihydrochloride). Trolox, a water soluble vitamin E analog, serves as positive control inhibition fluorescein decay in a dose dependent manner.

Matrix Metalloproteinase 1 Enzyme Activity (MMP1) Assay:

An in vitro matrix metalloprotease (MMP) inhibition assay. MMPs are extracellular proteases that play a role in many normal and disease states by virtue of their broad substrate specificity. MMP1 substrates include collagen IV. The Molecular Probes Enz/Chek Gelatinase/Collagenase Assay kit (#E12055) utilizes a fluorogenic gelatin substrate to detect MMP1 protease activity. Upon proteolytic cleavage, bright green fluorescence is revealed and may be monitored using a fluorescent microplate reader to measure enzymatic activity.

The Enz/Chek Gelatinase/Collagenase Assay kit (#E12055) from Invitrogen is designed as an in vitro assay to measure MMP1 enzymatic activity. The active ingredients, any one of the combination of ingredients, or compositions having said combinations disclosed in the specification can be assayed. The assay relies upon the ability of purified MMP1 enzyme to degrade a fluorogenic gelatin substrate. Once the substrate is specifically cleaved by MMP1 bright green fluorescence is revealed and may be monitored using a fluorescent microplate reader. Test materials are incubated in the presence or absence of the purified enzyme and substrate to determine their protease inhibitor capacity.

Cyclooxygenase (COX) Assay:

An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygnase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Lipoxygenase (LO) Assay:

An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotrienes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and the mixtures can be incubated for an additional 10 min at room temperature. Colorimetric substrate can be added to terminate catalysis and color progression can be evaluated by fluorescence plate reading at 490 nm. The percent inhibition of lipoxyganse activity can be calculated compared to non-treated controls to determine the ability of each of the active ingredients, any one of the combination of ingredients, or compositions having said combinations disclosed in the specification to inhibit the activity of purified enzyme.

Elastase Assay:

ENZCHEK® Elastase Assay (Kit #E-12056) from Molecular Probes (Eugene, Oreg. USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, N-methoxysuccinyl-Ala-Ala-Pro-Val-chloromethyl ketone, can be used as a selective, collective inhibitor of elastase when utilizing the EnzChek Elastase Assay Kit for screening for elastase inhibitors.

Oil Control Assay:

An assay to measure reduction of sebum secretion from sebaceous glands and/or reduction of sebum production from sebaceous glands can be assayed by using standard techniques known to those having ordinary skill in the art.

In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay:

An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay:

Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Clarity and Reduction in Freckles and Age Spots Assay:

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay:

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay:

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay:

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay With Methods Disclosed in Packman et al. (1978):

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer:

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer:

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas:

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Surface Contour of the Skin Assay with a Profilometer/Stylus Method:

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay:

In other non-limiting aspects, the efficacy of each of the active ingredients, any one of the combination of ingredients, or compositions having said combinations disclosed in the specification can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

Production of Filaggrin:

Changes in the production of filaggrin in keratinocytes due to each of the active ingredients, any one of the combination of ingredients, or compositions having said combinations disclosed in the specification can be measured. Filaggrin is the precursor to Natural Moisturizing Factor (NMF) in the skin. Increased NMF increases the moisture content of the skin. Filaggrin production in treated and non-treated keratinocytes can be determined using a bioassay that analyzes filaggrin concentration in keratinocyte cell lysates. A non-limiting example of a bioassay that can be used to quantify filaggrin production is the PROTEINSIMPLE® SIMONE™ western blotting protocol. For each sample, normal human epidermal keratinocytes (NHEK) are grown in EPI-200—Mattek EPILIFE® growth media with calcium from Life Technologies (M-EP-500-CA). NHEK are incubated in growth medium overnight at 37° C. in 5% $CO_2$ prior to treatment. NHEK are then incubated in growth medium with 1% test compound/extract or no compound/extract (negative control) for 24 to 36 hours. The NHEK can then be washed, collected, and stored on ice or colder until lysed on ice using a lysis buffer and sonication. The protein concentrations of the samples can be determined and used to normalize the samples. The lysates can be stored at −80° C. until use in the quantification assay.

The PROTEINSIMPLE® SIMON™ western blotting bioassay assay employs a quantitative western blotting immunoassay technique using an antibody specific for filaggrin to quantitatively detect filaggrin in the test samples. Cell samples are lysed and normalized for protein concentration. Normalized samples and molecular weight standards can then be loaded and ran on a denatured protein separation gel using capillary electrophoresis. The proteins in the gel are immobilized and immunoprobed using a primary antibody specific for filaggrin. The immobilized proteins can then be immunoprobed with an enzyme-linked detection antibody that binds the primary antibody. A chemiluminescent substrate solution can then be added to the immobilized proteins to allow chemiluminescent development in proportion to the amount of filaggrin bound in the immobilization. The chemiluminescent development is stopped at a specific time and the intensity of the chemiluminescent signal can be measured and compared to positive and negative controls.

Production of Occludin:

Changes in the production of occludin in keratinocytes due to each of the active ingredients, any one of the combination of ingredients, or compositions having said combinations disclosed in the specification can be measured. Occludin is a protein critical to the formulation of tight junctions and the skin's moisture barrier function. A non-limiting example of how occludin production in treated and non-treated keratinocytes can be determined is by the use of a bioassay that analyzes occludin concentration in keratinocyte cell lysates. The bioassay can be performed using PROTEINSIMPLE® SIMON™ western blotting protocol. For the samples, adult human epidermal keratinocytes (HEKa) from Life Technologies (C-005-5C) can be grown at 37° C. and 5% CO2 for 24 hours in Epilife growth media with calcium from Life Technologies (M-EP-500-CA) supplemented with Keratinocyte Growth Supplement (HKGS) from Life Technologies (S-101-5). HEKa are then incubated in growth medium with test compound/extract, no compound/extract for negative control, or with 1 mM $CaCl_2$ for positive control for 24 to 48 hours. The HEKa are then washed, collected, and stored on ice or colder until lysed on ice using a lysis buffer and sonication. The protein concentrations of the samples can be determined and used to normalize the samples. The lysates are stored at −80° C. until use in the bioassay.

The PROTEINSIMPLE® SIMON™ western blotting bioassay assay employs a quantitative western blotting immunoassay technique using an antibody specific for occludin to quantitatively detect occludin in the test samples. Cell samples are lysed and normalized for protein concentration. Normalized samples and molecular weight standards are then loaded and ran on a denatured protein separation gel using capillary electrophoresis. The proteins in the gel are then immobilized and immunoprobed using a primary antibody specific for occludin. The immobilized proteins are immunoprobed with an enzyme-linked detection antibody that binds the primary antibody. A chemiluminescent substrate solution is then added to the immobilized proteins to allow chemiluminescent development in proportion to the amount of occludin bound in the immobilization. The chemiluminescent development can be stopped at a specific time and the intensity of the chemiluminescent signal can be measured and compared to positive and negative controls.

Keratinocyte Monolayer Permeability:

Changes in the permeability of a keratinocyte monolayer due to each of the active ingredients, any one of the combination of ingredients, or compositions having said combinations disclosed in the specification can be measured. Keratinocyte monolayer permeability is a measure of skin barrier integrity. Keratinocyte monolayer permeability in treated and non-treated keratinocytes can be determined using, as a non-limiting example, the In Vitro Vascular Permeability assay by Millipore (ECM642). This assay analyzes endothelial cell adsorption, transport, and permeability. Briefly, adult human epidermal keratinocytes from Life Technologies (C-005-5C) can be seeded onto a porous collagen-coated membrane within a collection well. The keratinocytes are then incubated for 24 hours at 37° C. and 5% $CO_2$ in Epilife growth media with calcium from Life Technologies (M-EP-500-CA) supplemented with Keratinocyte Growth Supplement (HKGS) from Life Technologies (S-101-5). This incubation time allows the cells to form a monolayer and occlude the membrane pores. The media is then replaced with fresh media with (test sample) or without (non-treated control) test compounds/extracts and the keratinocytes are incubated for an additional 48 hours at 37° C. and 5% $CO_2$. To determine permeability of the keratinocyte monolayer after incubation with/without the test compound/extract, the media is replaced with fresh media containing a high molecular weight Fluorescein isothiocyanate (FITC)-Dextran and the keratinocytes are incubated for 4 hours at 37° C. and 5% $CO_2$. During the 4 hours incubation, FITC can pass through the keratinocytes monolayer and porous membrane into the collection well at a rate proportional to the monolayer's permeability. After the 4 hour incubation, cell viability and the content of FITC in the collection wells can be determined. For the FITC content, the media in the collection well is collected and fluorescence of the media determined at 480 nm (Em) when excited at 520 nm. Percent permeability and percent change in comparison to the non-treated controls can be determined by the following equations: Percent Permeability=((Mean Ex/Em of test sample)/Mean Ex/Em untreated control)*100; Percent Change=Percent Permeability of test sample−Percent Permeability of untreated control.

Production of Hyaluronic Acid:

Changes in the production of hyaluronic acid in human dermal fibroblasts due to each of the active ingredients, any one of the combination of ingredients, or compositions having said combinations disclosed in the specification can be measured. HA is a polysaccharide involved in stabilization of the structure of the matrix and is involved in providing turgor pressure to tissue and cells. As one non-limiting example, HA production in treated and non-treated adult human dermal fibroblasts (HDFa) cells can be determined using the Hyaluronan DuoSet ELISA kit from R&D Systems (DY3614). In this assay, for production of samples, subconfluent HDFa cells from Cascade Biologics (C-13-5C) are incubated at 37° C. and 10% $CO_2$ in starvation medium (0.15% fetal bovine serum and 1% Penicillin Streptomycin solution in Dulbecco's Modified Eagle Medium) for 72 hours prior to treatment. The cells are then incubated with fresh starvation medium with either test compound, positive control (phorbol 12-myristate 13-acetate from Sigma-Aldrich (P1585) and platelet derived growth factor from Sigma-Aldrich (P3201)), or no additive for 24 hours. Media is then collected and frozen at −80° C. until use in the ELISA assay.

Briefly, the ELISA assay employs a quantitative sandwich enzyme immunoassay technique whereby a capture antibody specific for HA can be pre-coated onto a microplate. Standards and media from treated and untreated cells are pipetted into the microplate wells to enable any HA present to be bound by the immobilized antibody. After washing away any unbound substances, an enzyme-linked detection antibody specific for HA is added to the wells. Following a wash to remove any unbound antibody-enzyme reagent, a substrate solution is added to the wells to allow color development in proportion to the amount of HA bound in the initial step. The color development is stopped at a specific time and the intensity of the color at 450 nm can be measured using a microplate reader.

Inhibition of Hyaluronidase Activity:

Changes in the activity of hyaluronidase due to each of the active ingredients, any one of the combination of ingredients, or compositions having said combinations disclosed in the specification can be measured. Hyaluronidase is an enzyme that degrades HA. HA is a polysaccharide involved in stabilization of the structure of the matrix and is involved in providing turgor pressure to tissue and cells. As one non-limiting example, hyaluronidase activity can be determined using an in vitro protocol modified from Sigma-Aldrich protocol #EC 3.2.1.35. Briefly, hyaluronidase type 1-S from Sigma-Aldrich (H3506) is added to microplate reaction wells containing test compound or controls. Tannic acid can be used as a positive control inhibitor, no test compound can be added for the control enzyme, and wells with test compound or positive control but without hyaluronidase can be used as a background negative control. The wells are incubated at 37° C. for 10 minutes before addition of substrate (HA). Substrate is added and the reactions incubated at 37° C. for 45 minutes. A portion of each reaction solution is then transferred to and gently mixed in a solution of sodium acetate and acetic acid pH 3.75 to stop that portion of the reaction (stopped wells). The stopped wells and the reaction wells should both contain the same volume of solution after addition of the portion of the reaction solution to the stopped wells. Both the reaction wells and the stopped wells are incubated for 10 minutes at room temperature. Absorbance at 600 nm is then measured for both the reaction wells and the stopped wells. Inhibition can be calculated using the following formulas: Inhibitor (or control) activity=(Inhibitor stopped wells absorbance at 600 nm−inhibitor reaction wells absorbance at 600 nm); Initial activity=control enzyme absorbance at 600 nm; Percent Inhibition=[(Initial activity/Inhibitor Activity)*100]−100.

Peroxisome Proliferator-Activated Receptor Gamma (PPAR-γ) Activity:

Changes in the activity of PPAR-γ due to each of the active ingredients, any one of the combination of ingredients, or compositions having said combinations disclosed in the specification can be measured. PPAR-γ is a receptor critical for the production of sebum. As one non-limiting example, the activity of PPAR-γ can be determined using a bioassay that analyzes the ability of a test compound or composition to inhibit binding of a ligand. Briefly, fluorescent small-molecule pan-PPAR ligand, FLUORMONE™ Pan-PPAR Green, available from Life Technologies (PV4894), can be used to determine if test compounds or compositions are able to inhibit binding of the ligand to PPAR-γ. The samples wells include PPAR-γ and fluorescent ligand and either: test compound or composition (test); a reference inhibitor, rosiglitazone (positive control); or no test compound (negative control). The wells are incubated for a set period of time to allow the ligand opportunity to bind the PPAR-γ. The fluorescence polarization of each sample well can then be measured and compared to the negative control well to determine the percentage of inhibition by the test compound or composition.

Cytokine Array:

Human epidermal keratinocytes are cultured to 70-80% confluency. The media in the plate is aspirated and 0.025% trypsin/EDTA is added. When the cells became rounded, the culture dish is gently tapped to release the cells. The trypsin/EDTA containing cells are removed from the culture dish and neutralized. Cells are centrifuged for 5 min. at 180×g to form a pellet of cells. The supernatant is aspirated. The resulting pellet is resuspended in EPILIFE™ media (Cascade Biologics). The cells are seeded in 6-well plates at approximately 10-20% confluency. After the cells became approximately 80% confluent, the media is aspirated and 1.0 ml of EPILIFE™, along with phorbol 13-Myristate 12-acetate ("PMA") (a known inducer of inflammation) and the test composition dilutions are added to two replicate wells (i.e., 1.0% (100 µl of 100× stock) and 0.1% (10 µl of 100× stock) test compositions are diluted into a final volume of 1 ml EpiLife Growth Medium). The media is gently swirled to ensure adequate mixing. In addition, 1.0 ml of EPILIFE™ is added to the control wells, with and without additional PMA. The plates are then incubated at 37±1° C. and 5.0±1% $CO_2$ for approximately 5 hours after dosing. Following this 5-hour incubation, all media is collected in conical tubes and frozen at −70° C.

For analysis, a 16-pad hybridization chamber is attached to 16-pad FAST slides arrayed in triplicate with 16 anti-cytokine antibodies plus experimental controls (Whatman BioSciences), and the slides are placed into a FASTFrame (4 slides per frame) for processing. Arrays are blocked for 15 min. at room temp. using 70 ml S&S Protein Array Blocking buffer (Whatman Schleicher and Scheull). Blocking buffer is removed and 70 ml of each supernatant sample is added to each array. Arrays are incubated for 3 hours at room temp. with gentle agitation. Arrays are washed 3 times with TBS-T. Arrays are treated with 70 ml of an antibody cocktail, containing one biotinylated antibody corresponding to each of the arrayed capture antibodies. Arrays are incubated for 1 hour at room temp. with gentle agitation. Arrays are washed 3 times with TBS-T. Arrays are incubated with 70 ml of a solution containing streptavidin-Cy5 conjugate for 1 hour at room temp. with gentle agitation. Arrays are washed 3 times with TBS-T, quickly rinsed in de-ionized water, and dried.

Slides can be imaged in a Perkin-Elmer ScanArray 4000 confocal fluorescent imaging system. Array images can be saved and analyzed using Imaging Research ArrayVision software. Briefly, spot intensities are determined by subtracting background signal. Spot replicates from each sample condition can be averaged and then compared to the appropriate controls.

Endothelial Tube Formation:

Endothelial tube formation is involved in angiogenesis and micro-vessel capillary formation. Capillary formation and angiogenesis may contribute to redness and rosacea of the skin. The ability for endothelial cells to form tubes in the presence or absence of test extracts and compounds may be determined using a capillary tubule disruption assay with pre-formed primary human umbilical vein endothelial cells (HUVEC) in a cell culture system.

Briefly, HUVECs are cultured in vitro on Extracellular Matrix, which stimulates the attachment and tubular morphogenesis of endothelial cells to form capillary-like lumen structures. These in vitro formed capillary tubules are similar to human blood vessel capillaries in many aspects. The capillary tube assay is based on this phenomenon and is used for evaluation of potential vasculature targeting agents.

HUVEC cultures are grown in a 5% $CO_2$ 37° C. cell incubator. The full growth medium for HUVECs is Endothelial Cell Basal Medium (EBM) supplemented with 2% fetal bovine serum (FBS), 12 µg/ml bovine brain extract, 1 µg/ml hydrocortisone, and 1 µg/ml GA-1000 (gentamicin-amphothericin). HUVEC cultures between passage 3 and 8 may be used for all assay experiments.

HUVECs are pre-labeled with fluorescent agent Calcein AM and seeded in Extracellular Matrix coated 96-well culture plate with their full growth medium. After about four hours of the morphogenesis process, the endothelial capillary tubes should be formed. Then, test agent in designed doses in 50 µl volume is applied into the formed capillary tubule cultures as treatment conditions. The no-treatment controls can be added with vehicle of test agents. Sutent, a FDA approved anti-angiogenic drug one concentration can be included as assay performance control. After about six hours of treatment, the endothelial tubule morphology in each well is examined by microscopy, imaged, and the capillary disrupting activities under treatment conditions can be quantitatively analyzed. Each test conditions can be conducted in duplicate wells, including controls.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of moisturizing skin, the method comprising topically applying to dry skin in need of moisturization a composition comprising an effective amount to moisturize skin of a combination of
    0.01 to 0.05% of an aqueous *Angelica acutiloba* root extract by weight of the composition,
    0.001 to 0.05% of a supercritical $CO_2$ *Salicornia herbacea* extract to increase aquaporin 3 expression and increase skin moisturization,
    0.001 to 2% niacinamide by weight of the composition, vegetable amino acids from navy bean extract, and
    0.001 to 1% hydrolyzed pearl extract by weight of the composition, wherein topically applying the composition to dry skin moisturizes the skin and increases expression of aquaporin 3 in the skin.

2. The method of claim 1, wherein the composition comprises 0.001 to 0.04% of the supercritical $CO_2$ *Salicornia herbacea* extract by weight of the composition and 0.001 to 1% niacinamide by weight of the composition.

3. The method of claim 1, wherein the composition further comprises an effective amount of sodium ascorbyl phosphate and/or ascorbyl glucoside to decrease tyrosinase activity in the skin, decrease melanin production in the skin, reduce oxidation of the skin, increase collagen-1 expression in the skin, increase lysyl oxidase in the skin, and/or reduce TNF-alpha and/or lipoxygenase activity in the skin.

4. The method of claim 1, wherein the composition further comprises 0.001 to 2% sodium ascorbyl phosphate and/or ascorbyl glucoside by weight of the composition.

5. The method of claim 1, wherein the composition further comprises 25 to 90% water by weight of the composition.

6. The method of claim 1, wherein the composition further comprises glycerin, butylene glycol, caprylic/capric triglyceride, acrylates/C10-30 alkyl acrylate crosspolymer, 1,2-hexanediol, and dimethicone.

7. The method of claim 1, wherein the composition is an emulsion, serum, gel, gel emulsion, gel serum, a cream, a cream-gel, a lotion, or a solution.

8. The method of claim 1, wherein the composition comprises 0.001 to 0.04% of the supercritical $CO_2$ *Salicornia herbacea* extract by weight.

9. The method of claim 1, wherein the composition comprises 0.001 to 1% niacinamide by weight of the composition.

10. The method of claim 1, wherein the composition further comprises 0.001 to 2% sodium ascorbyl phosphate and/or ascorbyl glucoside by weight of the composition.

11. The method of claim 1, wherein the composition comprises an effective amount of vegetable amino acids from navy bean to reduce tyrosinase activity and/or reduce melanin production in the skin.

12. The method of claim 1, wherein the composition further comprises *Opuntia tuna* fruit extract.

13. The method of claim 12, wherein the composition comprises 0.0001 to 0.015% *Opuntia tuna* fruit extract by weight of the composition.

14. The method of claim 1, wherein the composition comprises 0.001 to 0.01% of the supercritical $CO_2$ *Salicornia herbacea* extract by weight of the composition.

* * * * *